United States Patent
Yamazaki et al.

(10) Patent No.: US 9,570,778 B2
(45) Date of Patent: Feb. 14, 2017

(54) ELECTROLYTIC SOLUTION, ELECTROCHEMICAL DEVICE, LITHIUM ION SECONDARY BATTERY, AND MODULE

(71) Applicant: DAIKIN INDUSTRIES, LTD., Osaka-shi, Osaka (JP)

(72) Inventors: Shigeaki Yamazaki, Settsu (JP); Hideo Sakata, Settsu (JP); Mayuko Taeda, Settsu (JP); Meiten Koh, Settsu (JP); Aoi Nakazono, Settsu (JP); Michiru Kagawa, Settsu (JP); Akiyoshi Yamauchi, Settsu (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 27 days.

(21) Appl. No.: 14/394,301

(22) PCT Filed: Apr. 12, 2013

(86) PCT No.: PCT/JP2013/061121
§ 371 (c)(1),
(2) Date: Oct. 14, 2014

(87) PCT Pub. No.: WO2013/157503
PCT Pub. Date: Oct. 24, 2013

(65) Prior Publication Data
US 2015/0086877 A1    Mar. 26, 2015

(30) Foreign Application Priority Data

Apr. 17, 2012  (JP) ................ 2012-094111
Mar. 4, 2013   (JP) ................ 2013-042313

(51) Int. Cl.
| | | |
|---|---|---|
| H01M 10/0569 | (2010.01) |
| H01M 10/0567 | (2010.01) |
| H01M 10/0568 | (2010.01) |
| H01M 10/0525 | (2010.01) |
| C07D 317/36 | (2006.01) |
| H01G 11/60 | (2013.01) |
| H01G 11/64 | (2013.01) |

(52) U.S. Cl.
CPC ........ H01M 10/0569 (2013.01); C07D 317/36 (2013.01); H01G 11/60 (2013.01); H01G 11/64 (2013.01); H01M 10/0525 (2013.01); H01M 10/0567 (2013.01); H01M 10/0568 (2013.01); *H01M 2300/0034* (2013.01); *Y02E 60/122* (2013.01)

(58) Field of Classification Search
CPC ............ H01M 10/0564; H01M 10/0565; H01M 10/0567; H01M 10/0568; H01M 10/0569; H01M 10/0525
See application file for complete search history.

(56) References Cited

U.S. PATENT DOCUMENTS

| | | | |
|---|---|---|---|
| 5,633,099 A | 5/1997 | Yokoyama et al. |
| 5,659,062 A | 8/1997 | Yokoyama et al. |
| 6,045,945 A | 4/2000 | Hamamoto et al. |
| 2003/0015995 A1* | 1/2003 | Tamura et al. ............... 320/162 |
| 2003/0087160 A1* | 5/2003 | Suzuki et al. ............... 429/327 |
| 2005/0227143 A1* | 10/2005 | Amine .................. H01M 6/166 |
| | | | 429/188 |
| 2006/0078801 A1 | 4/2006 | Yamaguchi et al. |
| 2009/0226808 A1* | 9/2009 | Hiwara et al. ............... 429/200 |
| 2009/0253044 A1 | 10/2009 | Nogi et al. |
| 2010/0104950 A1 | 4/2010 | Lamanna et al. |
| 2010/0310943 A1 | 12/2010 | Koh et al. |
| 2011/0123872 A1 | 5/2011 | Koh et al. |
| 2011/0183200 A1* | 7/2011 | Odani et al. .................. 429/200 |
| 2012/0100401 A1 | 4/2012 | Yasui et al. |
| 2015/0004501 A1 | 1/2015 | Koh et al. |
| 2015/0086876 A1 | 3/2015 | Taeda et al. |

FOREIGN PATENT DOCUMENTS

| | | |
|---|---|---|
| CN | 103858267 A | 6/2014 |
| EP | 2750238 A1 | 7/2014 |

(Continued)

OTHER PUBLICATIONS

Communication dated Dec. 8, 2015 from the European Patent Office in Application No. 13777680.3.

(Continued)

Primary Examiner — Anca Eoff
(74) Attorney, Agent, or Firm — Sughrue Mion, PLLC

(57) ABSTRACT

The present invention aims to provide an electrolyte solution for forming, for example, a secondary battery having excellent oxidation resistance and high-temperature storage characteristics; an electrochemical device such as a lithium-ion secondary battery that contains the electrolyte solution; and a module that contains the electrochemical device. The present invention provides an electrolyte solution containing a solvent and an electrolyte salt, wherein the solvent contains a fluorine-containing compound (A) represented by formula (1) shown below in an amount of 0.01 to 20% by mass, and a fluorine-containing compound (B) represented by formula (2) shown below in an amount of 10 to 80% by mass:

$$Rf^1OCOOR \quad (1)$$

wherein $Rf^1$ is a C1-C4 fluorine-containing alkyl group, and R is a C1-C4 non-fluorinated alkyl group, and $$Rf^2OCOORf^3 \quad (2)$$

wherein $Rf^2$ and $Rf^3$ are the same or different, and each is a C1-C4 fluorine-containing alkyl group.

12 Claims, No Drawings

(56) References Cited

FOREIGN PATENT DOCUMENTS

| | | |
|---|---|---|
| JP | 7-6786 A | 1/1995 |
| JP | 10-270076 A | 10/1998 |
| JP | 11-40195 A | 2/1999 |
| JP | 2004-14134 A | 1/2004 |
| JP | 2004-281185 A | 10/2004 |
| JP | 2006-114285 A | 4/2006 |
| JP | 3807459 B2 | 8/2006 |
| JP | 2006-331866 A | 12/2006 |
| JP | 4392726 B2 | 1/2010 |
| JP | 2010-514144 A | 4/2010 |
| JP | 2013/061123 A1 | 7/2013 |
| KR | 10-2011-0027765 A | 3/2011 |
| KR | 10-2015-0002716 A | 1/2015 |
| WO | 2007043526 A1 | 4/2007 |
| WO | 2013/051634 A1 | 4/2013 |

OTHER PUBLICATIONS

Communication dated Dec. 8, 2015 from the European Patent Office in Application No. 13777844.5.
International Search Report for PCT/JP2013/061121 dated Jul. 30, 2013 [PCT/ISA/210].
U.S. Appl. No. 14/394,284, Taeda et al., filed Oct. 14, 2014.
Communication dated Aug. 1, 2016 from U.S. Patent & Trademark Office in related U.S. Appl. No. 14/394,284.
International Search Report dated Jul. 30, 2013 in corresponding International Patent Application No. PCT/JP2013/061123.
International Preliminary Report on Patentability dated Oct. 21, 2014 from the International Bureau of WIPO in counterpart International Patent Application No. PCT/JP2013/061121.
International Preliminary Report on Patentability dated Oct. 21, 2014 from the International Bureau of WIPO in counterpart International Patent Application No. PCT/JP2013/061123.

* cited by examiner

ELECTROLYTIC SOLUTION, ELECTROCHEMICAL DEVICE, LITHIUM ION SECONDARY BATTERY, AND MODULE

CROSS REFERENCE TO RELATED APPLICATIONS

This application is a National Stage of International Application No. PCT/JP2013/061121, filed on Apr. 12, 2013, which claims priority from Japanese Patent Application Nos. 2012-094111, filed on Apr. 17, 2012, and 2013-042313, filed on Mar. 4, 2013, the contents of all of which are incorporated herein by reference in their entirety.

TECHNICAL FIELD

The present invention relates to an electrolyte solution, an electrochemical device, a lithium-ion secondary battery, and a module.

BACKGROUND ART

Along with a decrease in the weight and size of recent electronic devices, the development of lithium-ion secondary batteries having high energy density has been advanced. In addition, as the lithium-ion secondary batteries become applicable to a wider range of fields, there is an increasing demand for improved battery characteristics. In particular, in the case of in-vehicle use of the lithium-ion secondary batteries, the safety and battery characteristics will be more important in the future.

Unfortunately, the lithium-ion secondary batteries are insufficient in safety in the cases where, for example, the batteries are overcharged, internally short-circuited, and penetrated by a nail. Thus, the safety of the batteries must be higher in the case of in-vehicle use. Further, in the case of in-vehicle use, the voltage is required to be higher than that currently used in order to increase the capacity.

As a method for improving the safety and increasing the voltage of an electrolyte secondary battery, use of a fluorine-containing ether having a specific structure has been proposed (for example, see Patent Literature 1). However, in the case of the electrolyte secondary battery of Patent Literature 1, the discharge capacity unfortunately decreases when the battery is left in a high temperature environment or when the battery is repeatedly charged and discharged.

As a method for improving the cycle characteristics of the lithium-ion secondary battery, it has been proposed to set the amount of alcohol in an electrolyte solution to less than 50 ppm (for example, see Patent Literature 2). Patent Literature 2 discloses the following: HF is generated as a result of a gradual reaction at room temperature between a fluorine-containing electrolyte solution and a diol or monoalcohol contained in a high-permittivity solvent such as ethylene carbonate or in a low viscosity solvent such as dimethyl carbonate; and such a reaction causes an increase in the amount of HF in the electrolyte solution along with the time, leading to a decrease in the battery cycle characteristics.

In addition, in order to provide a highly stable electrolyte solution having excellent withstand voltage and charge-discharge cycle characteristics as well as a high flash point, there has been proposed an electrolyte solution having an carbonate ester represented by formula [I]

[Chem. 1]

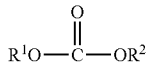

[I]

wherein $R^1$ represents an alkyl group or halogenated alkyl group; and $R^2$ represents an alkyl group or halogenated alkyl group not having a hydrogen atom at the position β (for example, see Patent Literature 3).

In addition, in order to provide an electrolyte solution having excellent safety, high conductivity, and low viscosity, and to provide an electrolyte secondary battery containing the electrolyte solution, there has been proposed an electrolyte solution containing [A] and [B], the [A] being a solvent containing a fluorinated carbonate, a cyclic carbonate, and a chain carbonate, wherein (i) the cyclic carbonate content is 2 to 63 mol %, (ii) the chain carbonate content is 2 to 63 mol %, and (iii) the fluorinated carbonate content is 60 to 96 mol % (provided that the total amount of (i) to (iii) does not exceed 100 mol %), and the fluorinated carbonate is a compound represented by the following formula [1]:

[Chem. 2]

[1]

wherein $R^1$ and $R^2$ may be the same or different; one of them is a C1-C4 hydrocarbon group in which at least one hydrogen atom is replaced by a fluorine atom; the other one is a C1-C4 hydrocarbon group or a C1-C4 hydrocarbon group in which at least one hydrogen atom is replaced by a fluorine atom; and these hydrocarbon groups include a group containing a heteroatom such as oxygen and nitrogen; and [B] an electrolyte (for example, see Patent Literature 4).

CITATION LIST

Patent Literature

Patent Literature 1: Japanese Patent No. 3807459
Patent Literature 2: JP-A H10-270076
Patent Literature 3: JP-A H07-6786
Patent Literature 4: Japanese Patent No. 4392726

SUMMARY OF INVENTION

Technical Problem

The present invention aims to provide an electrolyte solution for forming, for example, a secondary battery having excellent oxidation resistance and high-temperature storage characteristics; an electrochemical device such as a lithium-ion secondary battery that contains the electrolyte solution; and a module that contains the electrochemical device.

Solution to Problem

As a result of various studies to solve the above problem, the present inventors found that the high-temperature storage characteristics can be improved by an electrolyte solution containing a specific fluorine-containing compound, and accomplished the present invention.

Specifically, the present invention provides an electrolyte solution containing a solvent and an electrolyte salt, wherein the solvent contains a fluorine-containing compound (A) represented by formula (1) shown below in an amount of 0.01 to 20% by mass, and a fluorine-containing compound (5) represented by formula (2) shown below in an amount of 10 to 80% by mass, $$Rf^1OCOOR \tag{1}$$

wherein $Rf^1$ is a C1-C4 fluorine-containing alkyl group, and R is a C1-C4 non-fluorinated alkyl group, and $$Rf^2OCOORf^3 \tag{2}$$

wherein $Rf^2$ and $Rf^3$ are the same or different, and each is a C1-C4 fluorine-containing alkyl group.

Preferably, the fluorine-containing compound (A) is at least one compound selected from the group consisting of $CF_3CH_2OCOOCH_3$ and $CF_3CH_2OCOOC_2H_5$, and the fluorine-containing compound (B) is $CF_3CH_2OCOOCH_2CF_3$.

The solvent may further contain at least one selected from the group consisting of a non-fluorinated saturated cyclic carbonate, a fluorinated saturated cyclic carbonate, and a non-fluorinated chain carbonate.

The non-fluorinated saturated cyclic carbonate is preferably at least one compound selected from the group consisting of ethylene carbonate, propylene carbonate, and butylene carbonate.

The non-fluorinated chain carbonate is preferably at least one compound selected from the group consisting of dimethyl carbonate, ethyl methyl carbonate, diethyl carbonate, methyl propyl carbonate, methyl butyl carbonate, ethyl propyl carbonate, and ethyl butyl carbonate.

The mass ratio A/B of the fluorine-containing compound (A) to the fluorine-containing compound (B) is preferably less than 1.

The electrolyte salt is preferably at least one lithium salt selected from the group consisting of $LiPF_6$, $LiBF_4$, $LiSO_3CF_3$, $LiN(SO_2CF_3)_2$, $LiN(SO_2C_2F_5)_2$, lithium difluoro(oxalato)borate, lithium bis(oxalato)borate, and a salt represented by a formula: $LiPF_a(C_nF_{2n+1})_{6-a}$ wherein a is an integer of 0 to 5, and n is an integer of 1 to 6.

The electrolyte solution preferably contains 0.5 to 70 ppm of HF.

Preferably, the electrolyte solution further contains at least one compound selected from the group consisting of an unsaturated cyclic carbonate, a fluorinated saturated cyclic carbonate, and a cyclic sulfonic acid compound, in an amount of 0.1 to 10% by mass.

The present invention further provides an electrochemical device containing the above-described electrolyte solution.

The present invention still further provides a lithium-ion secondary battery containing the above-described electrolyte solution.

The present invention yet still further provides a module including the above-described electrochemical device or the above-described lithium-ion secondary battery.

The present invention is described in detail below.

Advantageous Effects of Invention

The present invention provides an electrolyte solution for forming an electrochemical device such as a lithium-ion secondary battery having excellent oxidation resistance and high-temperature storage characteristics.

DESCRIPTION OF EMBODIMENTS

The present invention relates to an electrolyte solution containing a solvent and an electrolyte salt, wherein the solvent contains a fluorine-containing compound (A) represented by formula (1) shown below in an amount of 0.01 to 20% by mass, and a fluorine-containing compound (B) represented by formula (2) shown below in an amount of 10 to 80% by mass:

$$Rf^1OCOOR \tag{1}$$

wherein $Rf^1$ is a C1-C4 fluorine-containing alkyl group, and R is a C1-C4 non-fluorinated alkyl group, and $$Rf^2OCOORf^3 \tag{2}$$

wherein $Rf^2$ and $Rf^3$ are the same or different, and each is a C1-C4 fluorine-containing alkyl group.

The electrolyte solution of the present invention contains a solvent and an electrolyte salt, wherein the solvent contains the fluorine-containing compound (A) represented by the above formula (1) and the fluorine-containing compound (B) represented by the above formula (2). Owing to these specific fluorine-containing compounds, the electrolyte solution can be made for use in electrochemical devices such as secondary batteries having excellent oxidation resistance and high-temperature storage characteristics, as well as electrochemical capacitors and electric double-layer capacitors.

In the fluorine-containing compound (A) represented by formula (1), $Rf^1$ is a C1-C4 fluorine-containing alkyl group.

The carbon number is preferably 1 to 3 for good compatibility with the electrolyte solution.

Examples of $Rf^1$ include $CF_3$—, $CF_3CF_2$—, $HCF_2CF_2$—, $(CF_3)_2CH$—, $CF_3CH_2$—, $C_2F_5CH_2$—, $HCF_2CF_2CH_2$—, and $CF_3CFHCF_2CH_2$—. Among these, $CF_3CH_2$— is preferred for high flame retardancy, good rate characteristics, and good oxidation resistance.

In the fluorine-containing compound (A) represented by formula (1), R is a C1-C4 non-fluorinated alkyl group.

The carbon number is preferably 1 to 3 for good compatibility with the electrolyte solution.

Examples of R include —$CH_3$, —$CH_2CH_3$, —$CH(CH_3)_2$, and —$C_3H_7$. Among these, —$CH_3$ and —$CH_2CH_3$ are preferred for low viscosity and good rate characteristics.

Specific examples of the fluorine-containing compound (A) represented by formula (1) include $CF_3CH_2OCOOCH_3$, $CF_3CH_2OCOOCH_2CH_3$, $CF_3CF_2CH_2OCOOCH_3$, and $CF_3CF_2CH_2OCOOCH_2CH_3$. Among these, at least one compound selected from the group consisting of $CF_3CH_2OCOOCH_3$ and $CF_3CH_2OCOOCH_2CH_3$ is preferred.

The fluorine-containing compound (A) is contained in an amount of 0.01 to 20% by mass in the solvent. If the amount of the fluorine-containing compound (A) is too small, the effects of the present invention may not be achieved. If the amount is too large, the battery characteristics may be impaired. The lower limit of the amount of the fluorine-containing compound (A) is preferably 0.02% by mass, and more preferably 0.03% by mass. The upper limit of the amount of the fluorine-containing compound (A) is preferably 15% by mass, more preferably 8% by mass, still more preferably 5% by mass, and particularly preferably 3% by mass.

In the fluorine-containing compound (B) represented by formula (2), $Rf^2$ and $Rf^3$ are the same or different, and each is a C1-C4 fluorine-containing alkyl group.

The carbon number is preferably 1 to 3 for good compatibility with the electrolyte solution.

Specific examples of $Rf^2$ and $Rf^3$ include the same fluorine-containing alkyl groups as mentioned for $Rf^1$. $Rf^2$ and Rf³ are preferably the same fluorine-containing alkyl group for stability of the compound.

Specific examples of the fluorine-containing compound (B) represented by formula (2) include $CF_3CH_2OCOOCH_2CF_3$, $CF_2HCF_2CH_2OCOOCH_2CF_2CF_2H$, and $(CF_3)_2CHOCOOCH(CF_3)_2$. Among these, $CF_3CH_2OCOOCH_2CF_3$ is more preferred.

According to the present invention, it was found that an electrolyte solution for forming a secondary battery having excellent oxidation resistance and high-temperature storage characteristics can be achieved by the addition of the fluorine-containing compound (A) and the fluorine-containing compound (B) to the electrolyte solution.

The fluorine-containing compound (B) is contained in an amount of 10 to 80% by mass in the solvent. If the amount of the fluorine-containing compound (B) is too small, the effects of the present invention may not be achieved. If the amount is too large, the battery characteristics may be impaired. The lower limit of the amount of the fluorine-containing compound (3) is preferably 20% by mass, and more preferably 30% by mass. The upper limit of the amount of the fluorine-containing compound (B) is preferably 75% by mass, and more preferably 70% by mass.

In the electrolyte solution of the present invention, the mass ratio A/B of the fluorine-containing compound (A) to the fluorine-containing compound (B) is preferably less than 1. The mass ratio A/B is more preferably 0.5 or less, and still more preferably 0.15 or less. At the same time, the mass ratio A/B is preferably 0.000001 or more, more preferably 0.001 or more, and still more preferably 0.005 or more.

The total amount of the fluorine-containing compounds (A) and (B) may be 10.01 to 100% by mass in the solvent. If the amount of the fluorine-containing compound is too small, the effects of the present invention may not be achieved. If the amount is too large, the battery characteristics may be impaired. The lower limit of the total amount of the fluorine-containing compounds (A) and (B) is more preferably 15% by mass, and still more preferably 20% by mass. The upper limit of the total amount of the fluorine-containing compounds (A) and (B) is more preferably 70% by mass, and still more preferably 65% by mass.

The solvent may further contain at least one selected from the group consisting of a non-fluorinated saturated cyclic carbonate, a fluorinated saturated cyclic carbonate, and a non-fluorinated chain carbonate. Alternatively, the solvent may contain at least one selected from the group consisting of a non-fluorinated saturated cyclic carbonate and a fluorinated saturated cyclic carbonate, and also a non-fluorinated chain carbonate. Still alternatively, the solvent may contain a fluorinated saturated cyclic carbonate and a non-fluorinated chain carbonate.

The solvent is preferably a non-aqueous solvent, and the electrolyte solution of the present invention is preferably a non-aqueous electrolyte solution.

Examples of the non-fluorinated saturated cyclic carbonate include ethylene carbonate (EC), propylene carbonate (PC), and butylene carbonate.

Among these, the non-fluorinated saturated cyclic carbonate is preferably at least one compound selected from the group consisting of ethylene carbonate, propylene carbonate, and butylene carbonate, for high permittivity and good viscosity.

The non-fluorinated saturated cyclic carbonate may be one of the above-mentioned compounds or a combination of two or more thereof.

The fluorinated saturated cyclic carbonate is a saturated cyclic carbonate having a fluorine atom. Specific examples include a fluorinated saturated cyclic carbonate (A) represented by the following formula (A)

[Chem. 3]

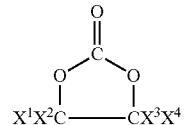

(A)

wherein $X^1$ to $X^4$ are the same or different, and each represents —H, —$CH_3$, —F, a fluorinated alkyl group optionally having an ether bond, or a fluorinated alkoxy group optionally having an ether bond, provided that at least one of $X^1$ to $X^4$ is —F, a fluorinated alkyl group optionally having an ether bond, or a fluorinated alkoxy group optionally having an ether bond.

Owing to the fluorinated saturated cyclic carbonate (A), when the electrolyte solution of the present invention is applied to a lithium-ion secondary battery or the like, a film that is stable to a negative electrode can be formed, and thus a side reaction of the electrolyte solution at the negative electrode can be sufficiently suppressed. As a result, very stable and excellent charge-discharge characteristics can be achieved.

The "ether bond" as mentioned herein is a bond represented by —O—.

In the above formula (A), one or two of $X^1$ to $X^4$ are each preferably —F, a fluorinated alkyl group optionally having an ether bond, or a fluorinated alkoxy group optionally having an ether bond, for good permittivity and oxidation resistance.

In the above formula (A), $X^1$ to $X^4$ are each preferably —H, —F, a fluorinated alkyl group (a), an ether bond-containing fluorinated alkyl group (b), or a fluorinated alkoxy group (c) for possibly achieving lower viscosity at a low temperature, a higher flash point, and improved solubility of the electrolyte salt.

The fluorinated alkyl group (a) is a group in which at least one hydrogen atom in an alkyl group is replaced by a fluorine atom. The carbon number of the fluorinated alkyl group (a) is preferably 1 to 20, more preferably 2 to 17, still more preferably 2 to 7, and particularly preferably 2 to 5.

If the carbon number is too large, the low-temperature characteristics may decrease, and the solubility of the electrolyte salt may decrease. If the carbon number is too small, it may result in problems such as a decrease in solubility of the electrolyte salt, a decrease in discharge efficiency, and an increase in viscosity.

Among the fluorinated alkyl groups (a), examples of fluorinated alkyl groups having a carbon number of 1 include $CFH_2$—, $CF_2H$—, and $CF_3$—.

Among the fluorinated alkyl groups (a), examples of preferred fluorinated alkyl groups having a carbon number of 2 or more include one represented by the following formula (a-1), for good solubility of the electrolyte salt:

$$R^1—R^2— \qquad \text{(a-1)}$$

wherein $R^1$ is a C1 or higher alkyl group optionally having a fluorine atom; and $R^2$ is a C1-C3 alkylene group optionally having a fluorine atom; provided that at least one of $R^1$ and $R^2$ has a fluorine atom.

$R^1$ and $R^2$ may further contain additional atoms other than carbon, hydrogen, and fluorine atoms.

$R^1$ is a C1 or higher alkyl group optionally having a fluorine atom. $R^1$ is preferably a C1-C16 linear or branched alkyl group. The carbon number of $R^1$ is more preferably 1 to 6, and still more preferably 1 to 3.

Specific examples of $R^1$ include the following linear or branched alkyl groups: $CH_3-$, $CH_3CH_2-$, $CH_3CH_2CH_2-$, $CH_3CH_2CH_2CH_2-$,

[Chem. 4]

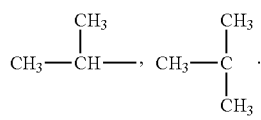

In the case where $R^1$ is a linear alkyl group having a fluorine atom, examples thereof include $CF_3-$, $CF_3CH_2-$, $CF_3CF_2-$, $CF_3CH_2CH_2-$, $CF_3CF_2CH_2-$, $CF_3CF_2CF_2-$, $CF_3CH_2CF_2-$, $CF_3CH_2CH_2CH_2-$, $CF_3CF_2CH_2CH_2-$, $CF_3CH_2CF_2CH_2-$, $CF_3CF_2CF_2CH_2-$, $CF_3CF_2CF_2CF_2-$, $CF_3CF_2CH_2CF_2-$, $CF_3CH_2CH_2CH_2CH_2-$, $CF_3CF_2CH_2CH_2CH_2-$, $CF_3CH_2CF_2CH_2CH_2-$, $CF_3CF_2CF_2CH_2CH_2-$, $CF_3CF_2CF_2CF_2CH_2-$, $CF_3CF_2CH_2CF_2CH_2$, $CF_3CF_2CH_2CH_2CH_2-$, $CF_3CF_2CF_2CF_2CH_2CH_2-$, $CF_3CF_2CH_2CF_2CH_2CH_2-$, $HCF_2-$, $HCF_2CH_2-$, $HCF_2CF_2-$, $HCF_2CH_2CH_2-$, $HCF_2CF_2CH_2-$, $HCF_2CH_2CF_2-$, $HCF_2CF_2CH_2CH_2-$, $HCF_2CH_2CF_2CH_2-$, $HCF_2CF_2CF_2CF_2-$, $HCF_2CF_2CH_2CH_2CH_2-$, $HCF_2CH_2CF_2CH_2CH_2-$, $HCF_2CF_2CF_2CF_2CH_2-$, $HCF_2CF_2CF_2CF_2CH_2CH_2-$, $FCH_2-$, $FCH_2CH_2-$, $FCH_2CF_2-$, $FCH_2CF_2CH_2-$, $FCH_2CF_2CF_2-$, $CH_3CF_2CH_2-$, $CH_3CF_2CF_2-$, $CH_3CH_2CH_2-$, $CH_3CF_2CH_2CF_2-$, $CH_3CF_2CF_2CF_2-$, $CH_3CH_2CF_2CF_2-$, $CH_3CF_2CH_2CF_2CH_2-$, $CH_3CF_2CF_2CF_2CH_2-$, $CH_3CF_2CF_2CH_2CH_2CH_2-$, $CH_3CH_2CF_2CF_2CH_2-$, $CH_3CF_2CH_2CF_2CH_2-$, $CH_3CF_2CH_2CF_2CH_2CH_2-$, $CH_3CF_2CF_2CF_2CH_2CH_2-$, $CH_3CF_2CH_2CF_2CH_2CH_2-$, $HCFClCF_2CH_2-$$HCF_2CFClCH_2-$, $HCF_2CFClCF_2CFClCH_2-$, and $HCFClCF_2CFClCF_2CH_2-$.

In addition, in the case where $R^1$ is a branched alkyl group having a fluorine atom, preferred examples thereof include the following:

[Chem. 5]

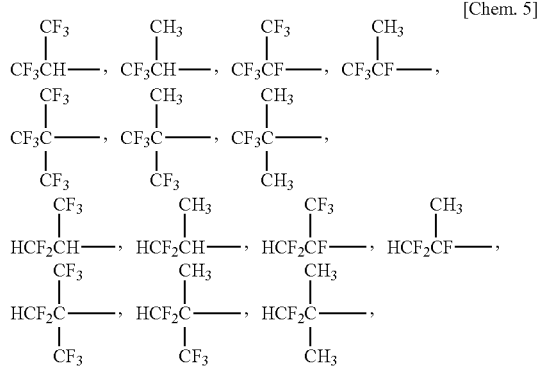

[Chem. 6]

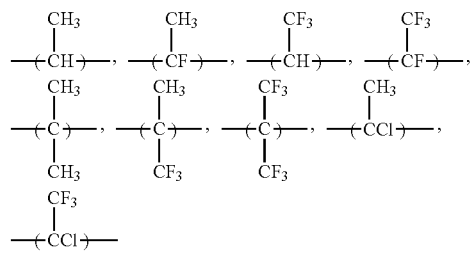

-continued $HCFCF_2CH_2-$, $HCF_2CFCH_2-$ (with $CF_3$ branch), $CH_3-CFCF_2-$ (with $CF_3$ branch), $CH_3CH_2-CFCF_2-$ (with $CF_3$ branch), $CH_3CH_2-CFCH_2-$ (with $CF_3$ branch), $HCFCH_2-$ (with $CF_3$ branch), $HCFCF_2-$ (with $CF_3$ branch), $HCF_2CF-$ (with $CF_3$ branch), $HCFCF_2CFCF_2CH_2-$ (with $CF_3$ branches), $HCF_2CFCF_2CFCH_2-$ (with $CF_3$ branches), $CH_3-C(CF_3)(CF_3)-CH_2-$.

Branches such as $-CH_3$ and $-CF_3$ tend to increase the viscosity. Thus, the number thereof is preferably small (i.e., 1), and more preferably zero.

$R^2$ is a C1-C3 alkylene group optionally having a fluorine atom. $R^2$ may be either linear or branched. Examples of minimum structural units constituting the above linear or branched alkylene groups are shown below. $R^2$ is formed from one minimum structural unit alone, or a combination of these minimum structural units.

(i) Linear minimum structural units:

$-CH_2-$, $-CHF-$, $-CF_2-$, $-CHCl-$, $-CFCl-$, $-CCl_2-$, (ii) Branched minimum structural units:

[Chem. 7]

$-(CH)-$ (with $CH_3$ branch), $-(CF)-$ (with $CH_3$ branch), $-(CH)-$ (with $CF_3$ branch), $-(CF)-$ (with $CF_3$ branch), $-(C)-$ (with $CH_3$, $CH_3$ branches), $-(C)-$ (with $CH_3$, $CF_3$ branches), $-(C)-$ (with $CF_3$, $CF_3$ branches), $-(CCl)-$ (with $CH_3$ branch), $-(CCl)-$ (with $CF_3$ branch)

Among the above examples, the structural units not containing Cl are preferred for avoiding a base-induced dehydrochlorination reaction and for ensuring higher safety.

In the case where $R^2$ is linear, it consists of the above-mentioned linear minimum structural unit, preferably $-CH_2-$, $-CH_2CH_2-$, or $CF_2-$. For further improving the solubility of the electrolyte salt, $-CH_2-$ or $-CH_2CH_2-$ is more preferred.

In the case where $R^2$ is branched, it includes at least one of the above mentioned branched minimum structural units, and preferred examples thereof include those represented by formula $-(CX^aX^b)-$ wherein $X^a$ is H, F, $CH_3$ or $CF_3$; and $X^b$ is $CH_3$ or $CF_3$; provided that in the case where $X^b$ is $CF_3$, $X^a$ is H or $CH_3$. These units can further improve the solubility of the electrolyte salt.

Examples of preferred fluorinated alkyl group (a) include $CF_3CF_2-$, $HCF_2CF_2-$, $H_2CFCF_2-$, $CH_3CF_2-$, $CF_3CF_2CF_2-$, $HCF_2CF_2CF_2-$, $H_2CFCF_2CF_2-$, $CH_3CF_2CF_2-$,

[Chem. 8]

$CF_3CH-$, $CF_3CH-$, $CF_3CF-$, $CF_3C-$,
(with CF₃, CH₃, CH₃, CH₃ groups above; CF₃ below the last)

$CF_3C-$, $HCF_2CH-$, $HCF_2CH-$, $HCF_2CF-$,
(with CH₃, CH₃, CF₃, CH₃ above; CH₃ below first)

$HCF_2C-$, $HCF_2C-$,
(with CH₃ above, CF₃ below; and CH₃ above, CH₃ below)

[Chem. 9]

$CF_3-CF-$, $CFCF_2CF_2-$, $CF_3-C-$.
(with CF₃ above each; CF₃ below first and third)

The ether bond-containing fluorinated alkyl group (b) is an ether bond-containing alkyl group in which at least one hydrogen atom is replaced by a fluorine atom. The carbon number of the ether bond-containing fluorinated alkyl group (b) is preferably 2 to 17. If the carbon number is too large, the fluorinated saturated cyclic carbonate (A) will have high viscosity and a large amount of fluorine-containing groups, resulting in low permittivity. As a result, the solubility of the electrolyte salt may decrease and the compatibility with other solvents may also decrease. In view of the above, the carbon number in the ether bond-containing fluorinated alkyl group (b) is more preferably 2 to 10, and still more preferably 2 to 7.

In the ether bond-containing fluorinated alkyl group (b), an alkylene group constituting the ether portion may be a linear or branched alkylene group. Examples of minimum structural units constituting the above linear or branched alkylene groups are shown below.

(i) Linear minimum structural units:
—$CH_2$—, —$CHF$—, —$CF_2$—, —$CHCl$—, —$CFCl$—, and —$CCl_2$—.

(ii) Branched minimum structural units:

[Chem. 10]

—(CH)—, —(CF)—, —(CH)—, —(CF)—,
(with CH₃, CH₃, CF₃, CF₃ above; CH₃, CH₃, CF₃, CH₃ below)

—(C)—, —(C)—, —(C)—, —(CCl)—,
(with CH₃, CH₃, CF₃, CH₃ above; CH₃, CF₃, CF₃ below)

—(CCl)—
(with CF₃ above)

An alkylene group may be formed from one minimum structural unit alone, a combination of plural linear units (i), a combination of plural branched units (ii), or a combination of a linear unit (i) and a branched unit (ii). Specific preferred examples are described later.

Among the above examples, the structural units not containing Cl are preferred for avoiding a base-induced dehydrochlorination reaction and for ensuring higher safety.

Examples of further preferred ether bond-containing fluorinated alkyl group (b) include those represented by formula (b-1):

$$R^3-(OR^4)_{n1}- \quad (b\text{-}1)$$

wherein $R^3$ is preferably a C1-C6 alkyl group optionally having a fluorine atom; $R^4$ is preferably a C1-C4 alkylene group optionally having a fluorine atom; and n1 is an integer of 1 to 3; provided that at least one of $R^3$ and $R^4$ includes a fluorine atom.

Examples of $R^3$ and $R^4$ include but not limited to the following groups, and these can be suitably combined to form the ether bond-containing fluorinated alkyl group (b) represented by the above formula (b-1).

(1) $R^3$ is preferably an alkyl group represented by a formula: $X^c_3C-(R^5)_{n2}-$ wherein three $X^c$ are the same or the different, and each is H or F; $R^5$ is a C1-5 alkylene group optionally having a fluorine atom; and n2 is 0 or 1.

In the case where n2 is 0, examples of $R^3$ include $CH_3-$, $CF_3-$, $HCF_2-$, and $H_2CF-$.

In the case where n2 is 1, specific examples of linear $R^3$ include $CF_3CH_2-$, $CF_3CF_2-$, $CF_3CH_2CH_2-$, $CF_3CF_2CH_2-$, $CF_3CF_2CF_2-$, $CF_3CH_2CF_2-$, $CF_3CH_2CH_2CH_2-$, $CF_3CF_2CH_2CH_2-$, $CF_3CH_2CF_2CH_2-$, $CF_3CF_2CF_2CH_2-$, $CF_3CF_2CF_2CF_2-$, $CF_3CF_2CH_2CF_2-$, $CF_3CH_2CH_2CH_2CH_2-$, $CF_3CF_2CH_2CH_2CH_2-$, $CF_3CH_2CF_2CH_2CH_2-$, $CF_3CF_2CF_2CH_2CH_2-$, $CF_3CF_2CH_2CF_2CH_2-CF_3CF_2CH_2CH_2CH_2CH_2-$, $CF_3CF_2CF_2CF_2CH_2CH_2-$, $CF_3CF_2CH_2CF_2CH_2CH_2-$ $HCF_2CH_2-$, $HCF_2CF_2-$, $HCF_2CH_2CH_2-$, $HCF_2CF_2CH_2-$, $HCF_2CH_2CF_2-$, $HCF_2CF_2CH_2CH_2-$, $HCF_2CH_2CF_2CH_2-$, $HCF_2CF_2CF_2CF_2-$, $HCF_2CF_2CH_2CH_2CH_2-$, $HCF_2CH_2CF_2CH_2CH_2-$, $HCF_2CF_2CF_2CF_2CH_2-$, $HCF_2CF_2CF_2CF_2CH_2CH_2-$, $FCH_2CH_2-$, $FCH_2CF_2-$, $FCH_2CF_2CH_2-$, $FCH_2CF_2CH_2-$, $CH_3CF_2-$, $CH_3CH_2-$, $CH_3CF_2CH_2-$, $CH_3CF_2CF_2-$, $CH_3CH_2CH_2-$, $CH_3CF_2CH_2CF_2$, $CH_3CF_2CF_2CF_2-$, $CH_3CH_2CF_2CF_2CH_3CH_2CH_2CH_2-$, $CH_3CF_2CH_2CF_2CH_2CH_3CF_2CF_2CF_2CH_2-$, $CH_3CF_2CF_2CH_2CH_2-$, $CH_3CH_2CF_2CF_2CH_2-$, $CH_3CF_2CH_2CF_2CH_2-$, $CH_3CH_2CF_2CH_2CH_2-$, $CH_3CH_2CF_2CF_2CH_2CH_2-$, and $CH_3CF_2CH_2CF_2CH_2CH_2-$.

Examples of branched $R^3$ wherein n2 is 1 include

[Chem. 11]

$CF_3CH-$, $CF_3CH-$, $CF_3CF-$, $CF_3CF-$,
(with CF₃, CH₃, CF₃, CH₃ above; CF₃, CH₃, CH₃, CH₃ below)

$CF_3C-$, $CF_3C-$, $CF_3C-$, $CF_3-C-CH_2-$,
(with CF₃, CH₃, CF₃, CF₃ above; CF₃, CF₃, CH₃, CF₃ below)

$HCF_2CH-$, $HCF_2CH-$, $HCF_2CF-$, $HCF_2CF-$,
(with CF₃, CH₃, CF₃, CH₃ above; CF₃, CH₃, CH₃, CH₃ below)

$HCF_2C-$, $HCF_2C-$, $HCF_2C-$.
(with CF₃, CH₃, CH₃ above; CF₃, CF₃, CH₃ below)

Branches such as —$CH_3$ and —$CF_3$ tend to increase the viscosity. Thus, $R^3$ being linear is more preferred.

(2) In the above formula (b-1), n1 in —$(OR^4)_{n1}$— is an integer of 1 to 3, and preferably 1 or 2. When n1=2 or 3, each $R^4$ may be the same or different.

Specific examples of preferred $R^4$ may include the following linear or branched groups.

Examples of linear groups include —$CH_2$—, —CHF—, —$CF_2$—, —$CH_2CH_2$—, —$CF_2CH_2$—, —$CF_2CF_2$—, —$CH_2CF_2$—, —$CH_2CH_2CH_2$—, —$CH_2CH_2CF_2$—, —$CH_2CF_2CH_2$—, —$CH_2CF_2CF_2$—, —$CF_2CH_2CH_2$—, —$CF_2CF_2CH_2$—, —$CF_2CH_2CF_2$—, and —$CF_2CF_2CF_2$—.

Examples of branched groups include

[Chem. 12]

$$\begin{array}{cccc}
CF_3 & CH_3 & CF_3 & CH_3 \\
| & | & | & | \\
-CH-, & -CH-, & -CF-, & -CF-, \\
| & | & | & | \\
CF_3 & CH_3 & CH_3 & CF_3
\end{array}$$

$$\begin{array}{cccc}
CF_3 & CH_3 & CF_3 & \\
| & | & | & \\
-C-, & -C-, & -C-, & -CFCF_2-, \\
| & | & | & \\
CF_3 & CF_3 & CH_3 &
\end{array}$$

$$\begin{array}{ccc}
CF_3 & CF_3 & CH_3 \\
| & | & | \\
-CFCH_2-, & -CHCH_2-, & -CHCH_2-, \\
CH_3 & CH_3 & CH_3 \\
| & | & | \\
-CFCH_2-, & -CFCF_2-, & -CHCF_2-, \\
CF_3 & & \\
| & & \\
-CHCF_2-. & &
\end{array}$$

The fluorinated alkoxy group (c) is an alkoxy group in which at least one hydrogen atom is replaced by a fluorine atom. The carbon number of the fluorinated alkoxy group (c) is preferably 1 to 17. The carbon number is more preferably 1 to 6.

The fluorinated alkoxy group (c) is particularly preferably a fluorinated alkoxy group represented by a formula: $X^d_3C$—$(R^6)_{n3}$—O— wherein three $X^d$s are the same or different, and each is H or F; $R^6$ is preferably a C1-C5 alkylene group optionally having a fluorine atom; and n3 is 0 or 1; provided that at least one of three $X^d$s contains a fluorine atom.

Specific examples of the fluorinated alkoxy group (c) include a fluorinated alkoxy group which is the alkyl group exemplified as $R^1$ in the above formula (a-1) terminated with an oxygen atom.

In the fluorinated saturated cyclic carbonate (A), the fluorine content in each of the fluorinated alkyl group (a), ether bond-containing fluorinated alkyl group (b), and fluorinated alkoxy group (c) is preferably 10% by mass or more. If the fluorine content is too low, an effect of decreasing the viscosity at a low temperature and an effect of increasing the flash point may not be sufficiently achieved. In view of the above, the fluorine content is more preferably 12% by mass or more, and still more preferably 15% by mass or more. The upper limit is usually 76% by mass.

The fluorine content in each of the fluorinated alkyl group (a), the ether bond-containing fluorinated alkyl group (b), and the fluorinated alkoxy group (c) is a value calculated from the following formula, based on the structural formula of each group: {(Number of fluorine atoms×19)/Formula weight of each group}×100(%).

In addition, for good permittivity and oxidation resistance, the total fluorine content in the fluorinated saturated cyclic carbonate (A) is preferably 10% by mass or more, and more preferably 15% by mass or more. The upper limit is usually 76% by mass.

The fluorine content in the fluorinated saturated cyclic carbonate (A) is a value calculated from the following formula, based on the structural formula of the fluorinated saturated cyclic carbonate (A): {(Number of fluorine atoms× 19)/Molecular weight of the fluorinated saturated cyclic carbonate (A)}×100(%).

Specific examples of the fluorinated saturated cyclic carbonate (A) include the following:

In the above formula (A), specific examples of the fluorinated saturated cyclic carbonate (A) in which at least one of $X^1$ to $X^4$ is —F include:

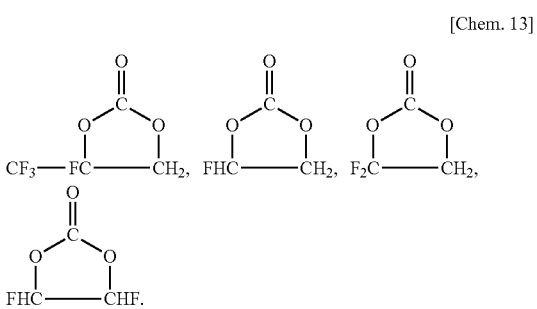

[Chem. 13]

These compounds have high withstand voltage, and the solubility of the electrolyte salt is also good.

In addition, those shown below are also usable:

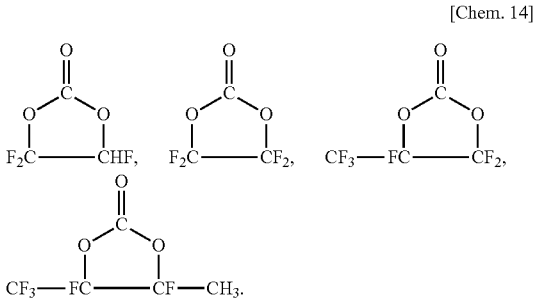

[Chem. 14]

In the above formula (A), specific examples of the fluorinated saturated cyclic carbonate (A) wherein at least one of $X^1$ to $X^4$ is the fluorinated alkyl group (a) and the others are —H include:

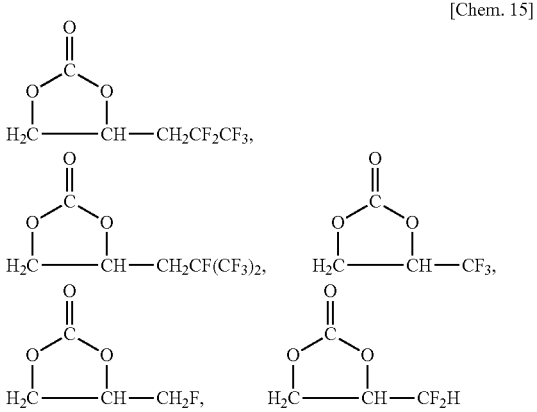

[Chem. 15]

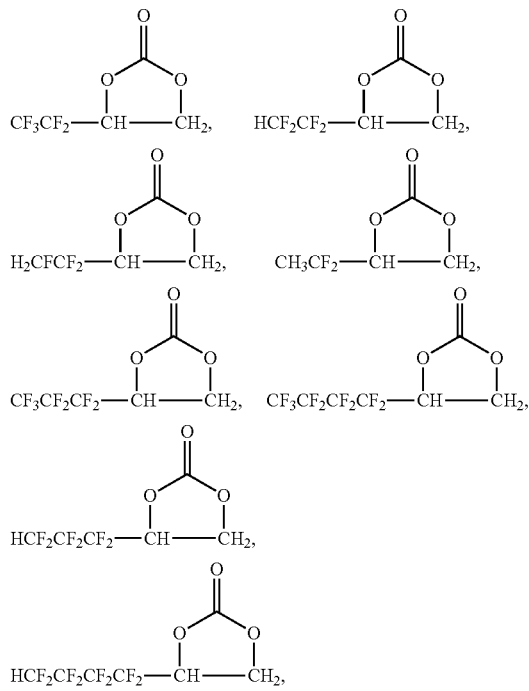
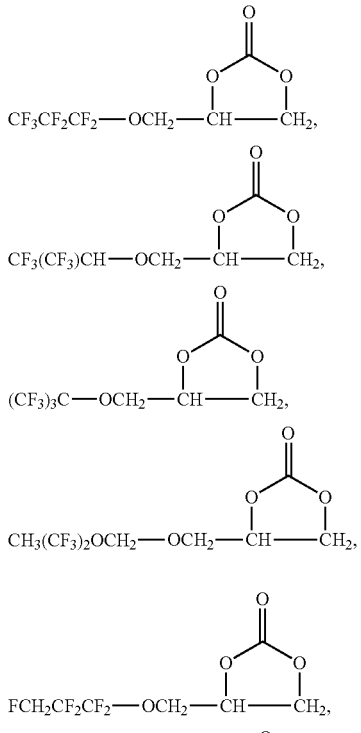
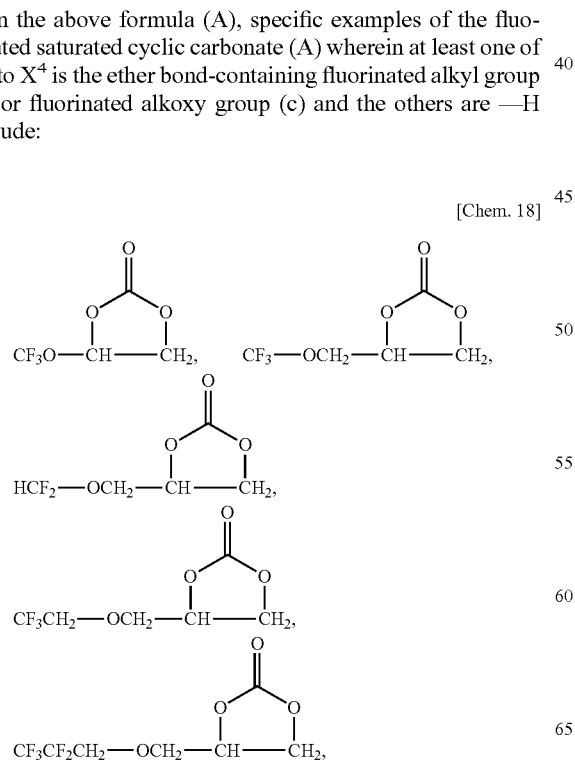
In the above formula (A), specific examples of the fluorinated saturated cyclic carbonate (A) wherein at least one of $X^1$ to $X^4$ is the ether bond-containing fluorinated alkyl group (b) or fluorinated alkoxy group (c) and the others are —H include:
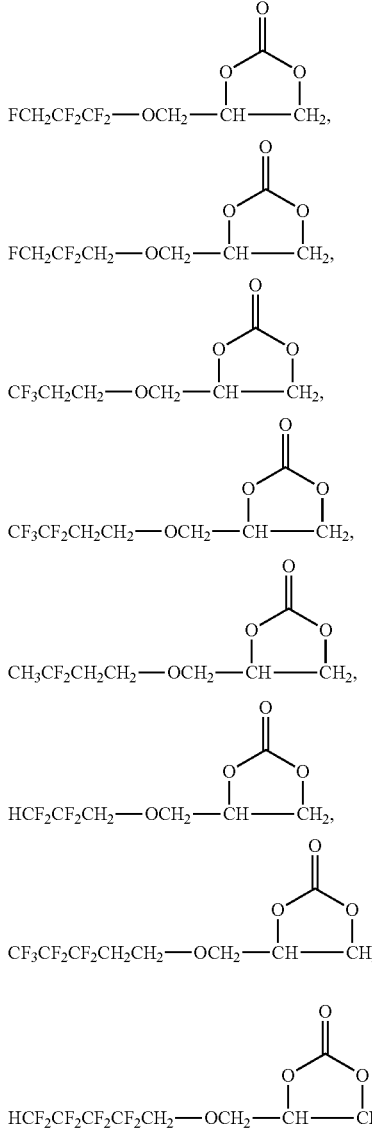

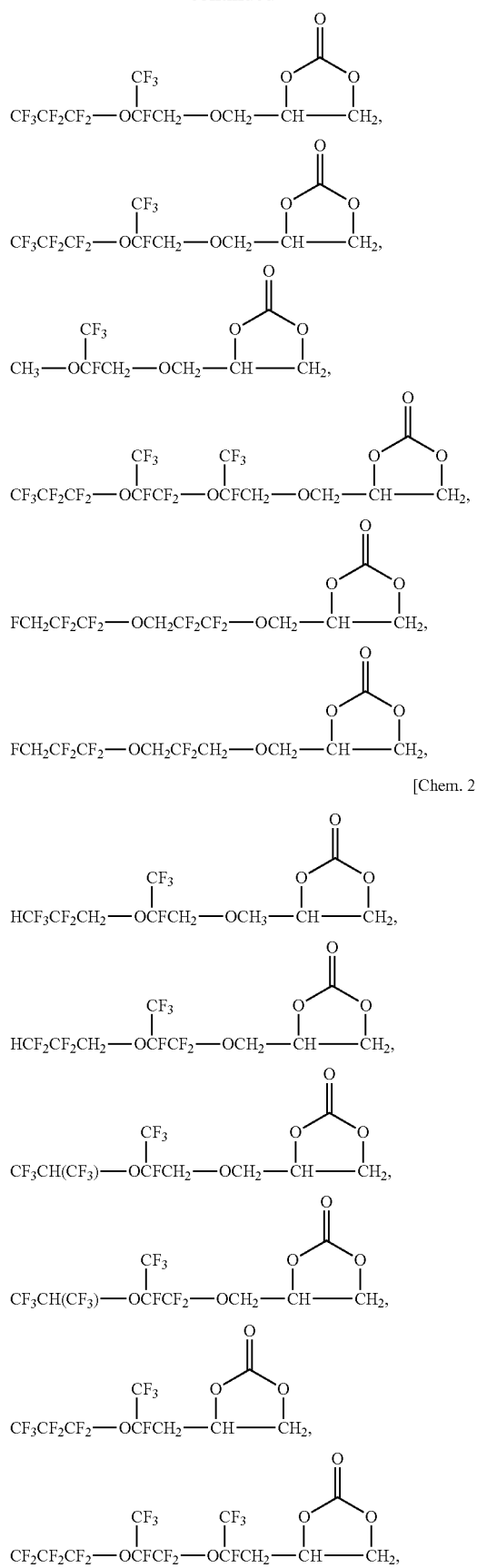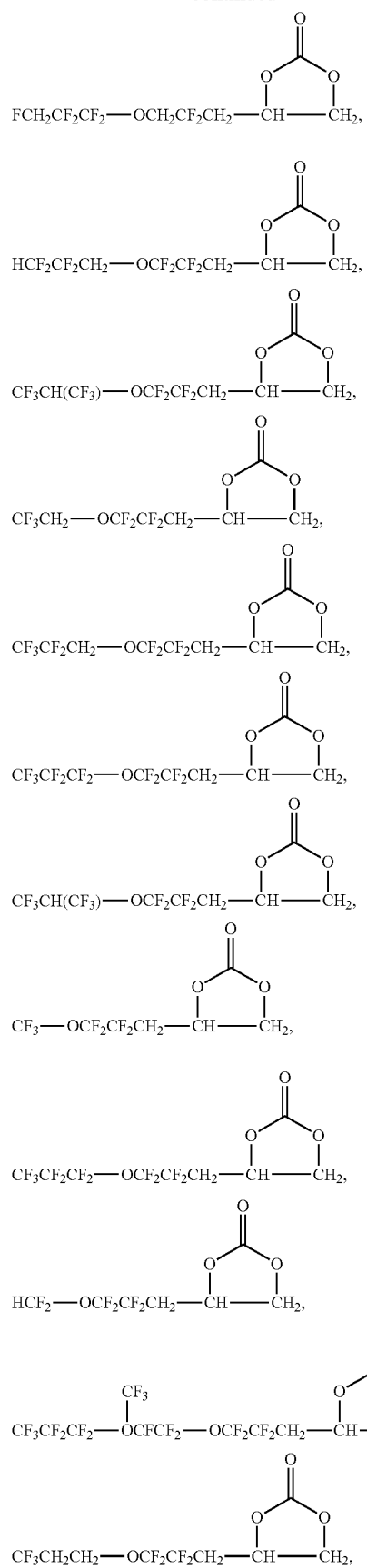

-continued

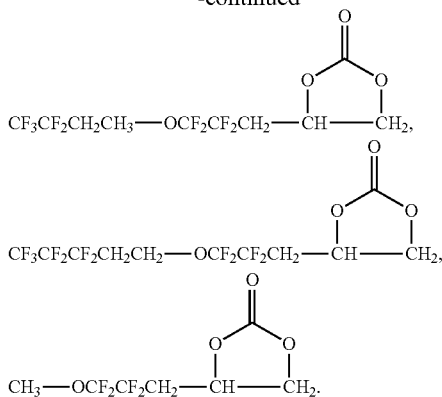

Examples of the fluorinated saturated cyclic carbonate (A) are not limited to the above specific examples. These examples of the fluorinated saturated cyclic carbonate (A) may be used alone or in any combination of two or more thereof at any ratio.

Among the examples of the fluorinated saturated cyclic carbonate (A), fluoroethylene carbonate and difluoroethylene carbonate are preferred.

Examples of the non-fluorinated chain carbonate include hydrocarbon-based chain carbonates such as $CH_3OCCOCH_3$ (dimethyl carbonate: DMC), $CH_3CH_2OCOOCH_2CH_3$ (diethyl carbonate: DEC), $CH_3CH_2OCOOCH_3$ (ethyl methyl carbonate: EMC), $CH_3OCOOCH_2CH_2CH_3$ (methyl propyl carbonate), methyl butyl carbonate, ethyl propyl carbonate, and ethyl butyl carbonate. Among these, the non-fluorinated chain carbonate is preferably at least one compound selected from the group consisting of dimethyl carbonate, ethyl methyl carbonate, diethyl carbonate, methyl propyl carbonate, methyl butyl carbonate, ethyl propyl carbonate, and ethyl butyl carbonate.

In the electrolyte solution of the present invention, the fluorine-containing compounds (A) and (B), non-fluorinated saturated cyclic carbonate, fluorinated saturated cyclic carbonate, and non-fluorinated chain carbonate are contained preferably in a total amount of 10 to 95% by mass, and more preferably 15 to 80% by mass in the electrolyte solution.

In the case where the solvent is a fluorinated saturated cyclic carbonate, the fluorinated saturated cyclic carbonate is contained preferably in an amount of 10.01 to 80% by mass, and more preferably 20 to 50% by mass in the electrolyte solution.

The electrolyte solution of the present invention contains an electrolyte salt.

The electrolyte salt may be any electrolyte salt that can be used in the electrolyte solution for a secondary battery. Yet, a lithium salt is preferred.

Examples of the lithium salt include inorganic lithium salts such as $LiClO_4$, $LiPF_6$, and $LiBF_4$; fluorine-containing organic acid lithium salts such as $LiSO_3CF_3$, $LiN(SO_2CF_3)_2$, $LiN(SO_2C_2F_5)_2$, $LiN(SO_2CF_3)(SO_2C_4F_9)$ $LiC(SO_2CF_3)^3$, $LiPF_4(CF_3)_2$, $LiPF_4(C_2F_5)_2$, $LiPF_4(SO_2CF_3)_2$, $LiPF_4(SO_2C_2F_5)_2$, $LiPF_2(CF_3)_2$, $LiBF_2(C_2F_5)_2$, $LiBF_2(SO_2CF_3)_2$, $LiBF_2(SO_2C_2F_5)_2$, lithium difluoro(oxalato)borate, lithium bis(oxalato)borate, and salts represented by the following formula: $LiPF_a(C_nF_{2n+1})_{6-a}$ wherein a is an integer of 0 to 5, and n is an integer of 1 to 6. These examples may be used alone or in combination of two or more thereof.

Among these, the lithium salt is preferably at least one selected from the group consisting of $LiPF_6$, $LiBF_4$, $LiSO_3CF_3$, $LiN(SO_2CF_3)_2$, $LiN(SO_2C_2F_5)_2$, lithium difluoro(oxalato)borate, lithium bis(oxalato)borate, and the salts represented by the following formula: $LiPF_a(C_nF_{2n+1})_{6-a}$ wherein a is an integer of 0 to 5, and n is an integer of 1 to 6, for suppressing deterioration of the electrolyte solution after high-temperature storage.

Examples of salts represented by the formula: $LiPF_a(C_nF_{2n+1})_{6-a}$ include $LiPF_3(CF_3)_3$, $LiPF_3(C_2F_5)_3$, $LiPF_3(C_3F_7)_3$, $LiPF_3(C_4F_9)$ $LiPF_4(CF_3)$ $LiPF_4(C_2F_5)_2$, $LiPF_4(C_3F_7)_2$, and $LiPF_4(C_4F_9)_2$ (provided that an alkyl group represented by $C_3F_7$ or $C_4F_9$ in the formula may be linear or branched).

The concentration of the electrolyte salt in the electrolyte solution is preferably 0.5 to 3 mol/L. If the concentration is outside of the range, the electrolyte solution tends to have low electrical conductivity, leading to poor battery performance.

The concentration of the electrolyte salt is more preferably 0.9 mol/L or more, and more preferably 1.5 mol/L or less.

The electrolyte salt for the electrolyte solution for an electric double-layer capacitor is preferably an ammonium salt.

Examples of the ammonium salt include (IIa) to (IIe) shown below.

(IIa) Tetraalkyl Quaternary Ammonium Salt

Preferred examples include a tetraalkyl quaternary ammonium salt represented by formula (IIa):

[Chem. 24]

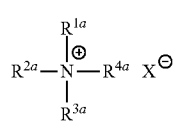

(IIa)

wherein $R^{1a}$, $R^{2a}$, $R^{3a}$, and $R^{4a}$ are the same or different, and each represents a C1-C6 alkyl group optionally having an ether bond; and $X^-$ is an anion. In addition, the same ammonium salt in which some or all of the hydrogen atoms are replaced by fluorine atoms and/or C1-C4 fluorine-containing alkyl groups is also preferred for improving oxidation resistance.

Specific examples include a tetraalkyl quaternary ammonium salt represented by formula (IIa-1):

[Chem. 25]

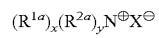

(IIa-1)

wherein $R^{1a}$, $R^{2a}$, and $X^-$ are as defined above; and x and y are the same or different, each is an integer of 0 to 4, and x+y=4. Examples also include an alkyl ether group-containing trialkyl ammonium salt represented by formula (IIa-2):

[Chem. 26]

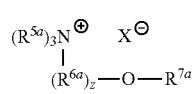

(IIa-2)

wherein $R^{5a}$ is a C1-C6 alkyl group; $R^{6a}$ is a C1-C6 divalent hydrocarbon group; $R^{7a}$ is a C1-C4 alkyl group; z is 1 or 2; and $X^-$ is an anion. Introduction of an alkyl ether group can reduce the viscosity.

The anion $X^-$ may be an inorganic anion or organic anion. Examples of inorganic anions include $AlCl_4^-$, $BF_4^-$, $PF_6^-$, $AsF_6^-$, $TaF_6^-$, $I^-$, and $SbF_6^-$. Examples of organic anions include $CF_3COO^-$, $CF_3SO_3^-$, $(CF_3SO_2)_2N^-$, and $(C_2F_5SO_2)_2N^-$.

Among these, $BF_4^-$, $PF_6^-$, $AsF_6^-$, and $SbF_6^-$ are preferred for good oxidation resistance and ionic dissociation.

Specific examples of preferred tetraalkyl quaternary ammonium salts include $Et_4NBF_4$, $Et_4NClO_4$, $Et_4NPF_6$, $Et_4NAsF_6$, $Et_4NSbF_6$, $Et_4NCF_3SO_3$, $Et_4N(CF_3SO_2)_2N$, $Et_4NC_4F_9SO_3$, $Et_3MeNBF_4$, $Et_3MeNClO_4$, $Et_3MeNPF_6$, $Et_3MeNAsF_6$, $Et_3MeNSbF_6$, $Et_3MeNCF_3SO_3$, $Et_3MeN(CF_3SO_2)_2N$, $Et_3MeNC_4F_9SO_3$, and N,N-diethyl-N-methyl-N-(2-methoxyethyl) ammonium salt. In particular, $Et_4NBF_4$, $Et_4NPF_6$, $Et_4NSbF_6$, $Et_4NAsF_6$, $Et_3MeNBF_4$, and N,N-diethyl-N-methyl-N-(2-methoxyethyl) ammonium salt are preferred.

(IIb) Spiro-Ring Bipyrrolidinium Salt

Preferred examples include a spiro-ring bipyrrolidinium salt represented by formula (IIb-1):

[Chem. 27]

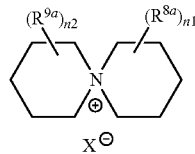

(IIb-1)

wherein $R^{8a}$ and $R^{9a}$ are the same or different, and each is a C1-C4 alkyl group; $X^-$ is an anion; n1 is an integer of 0 to 5; and n2 is an integer of 0 to 5;

a spiro-ring bipyrrolidinium salt represented by formula (IIb-2)

[Chem. 28]

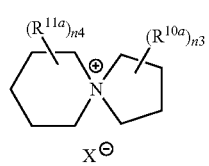

(IIb-2)

wherein $R^{10a}$ and $R^{11a}$ are the same or different, and each is a C1-C4 alkyl group; $X^-$ is an anion; n3 is an integer of 0 to 5; and n4 is an integer of 0 to 5; and a spiro-ring bipyrrolidinium salt represented by formula (IIb-3)

[Chem. 29]

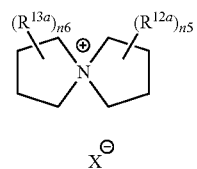

(IIb-3)

wherein $R^{12a}$ and $R^{13a}$ are the same or different, and each is a C1-C4 alkyl group; $X^-$ is an anion; n5 is an integer of 0 to 5; and n6 is an integer of 0 to 5. In addition, the same Spiro-ring bipyrrolidinium salt in which some or all of the hydrogen atoms are replaced by fluorine atoms and/or C1-C4 fluorine-containing alkyl groups is also preferred for improving oxidation resistance.

Specific examples of preferred anions $X^-$ are as mentioned above for (IIa). Among those examples, $BF_4^-$, $PF_6^-$, $(CF_3SO_2)_2N^-$, and $(C_2F_5SO_2)_2N^-$ are preferred for high dissociation ability and low internal resistance at a high voltage.

Specific examples of preferred spiro-ring bipyrrolidinium salts include

[Chem. 30]

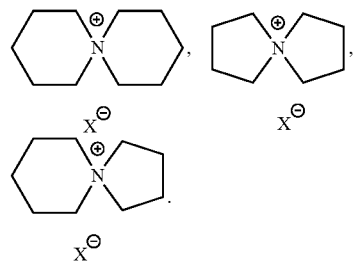

These spiro-ring bipyrrolidinium salts are excellent in terms of solubility in the solvent, oxidation resistance, and ionic conductivity.

(IIc) Imidazolium Salt

Preferred examples include an imidazolium salt represented by formula (IIc):

[Chem. 31]

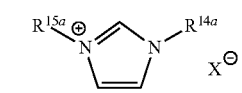

(IIc)

wherein $R^{14a}$ and $R^{15a}$ are the same or different, and each represents a C1-C6 alkyl group; and $X^-$ is an anion. In addition, the same imidazolium salt in which some or all of the hydrogen atoms are replaced by fluorine atoms and/or C1-C4 fluorine-containing alkyl groups is also preferred for improving oxidation resistance.

Specific examples of preferred anions $X^-$ are as mentioned above for (IIa).

Specific preferred examples include

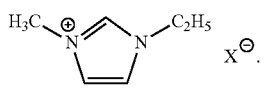

[Chem. 32]

The above imidazolium salt is excellent in terms of low viscosity and good solubility.

(IId): N-alkylpyridinium salt
Preferred examples include a N-alkylpyridinium salt represented by formula (IId):

[Chem. 33]

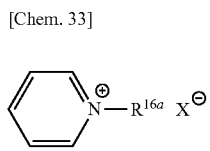

(IId)

wherein $R^{16a}$ is a C1-C6 alkyl group; and $X^-$ is an anion. In addition, the same N-alkylpyridinium salt in which some or all of the hydrogen atoms are replaced by fluorine atoms and/or C1-C4 fluorine-containing alkyl groups is also preferred for improving oxidation resistance.

Specific examples of preferred anions $X^-$ are as mentioned above for (IIa).

Preferred specific examples include

[Chem. 34]

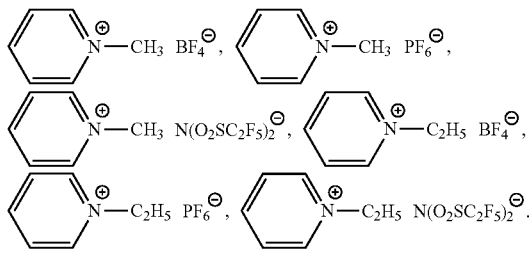

These N-alkylpyridinium salts are excellent in terms of low viscosity and good solubility.

(IIe) N,N-dialkylpyrrolidinium salt
Preferred examples include an N,N-dialkylpyrrolidinium salt represented by formula (IIe):

[Chem. 35]

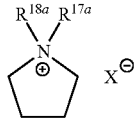

(IIe)

wherein $R^{17a}$ and $R^{18a}$ are the same or different, and each represents a C1-C6 alkyl group; and $X^-$ is an anion. In addition, the same N,N-dialkylpyrrolidinium salt in which some or all of the hydrogen atoms are replaced by fluorine atoms and/or C1-C4 fluorine-containing alkyl groups is also preferred for improving oxidation resistance.

Specific examples of preferred anions $X^-$ are as mentioned above for (IIa).

Specific preferred examples include

[Chem. 36]

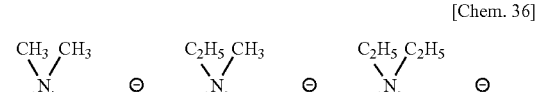

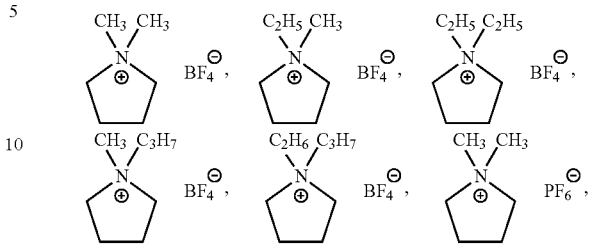

[Chem. 37]

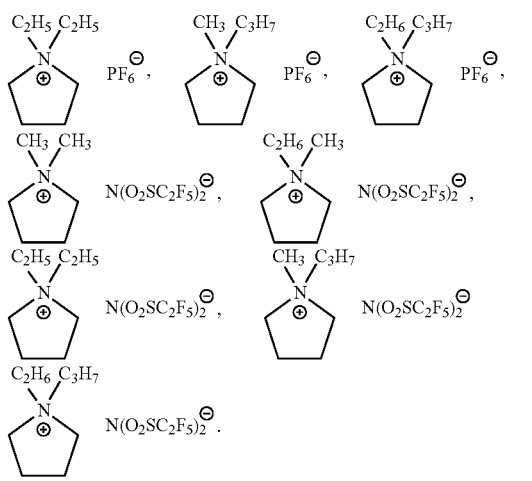

These N,N-dialkylpyrrolidinium salts are excellent in terms of low viscosity and good solubility.

Among these ammonium salts, (IIa), (IIb), and (IIc) are preferred for good solubility, oxidation resistance, and ionic conductivity. More preferred ammonium salts are shown below:

[Chem. 38]

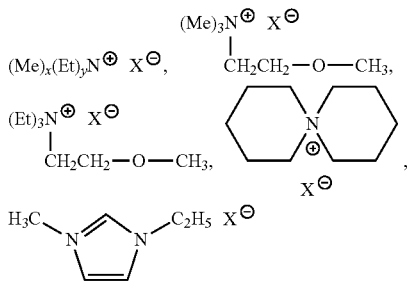

wherein Me is a methyl group; Et is an ethyl group; and $X^-$, x, and y are as defined above for formula (IIa-1).

In addition, a lithium salt may be used as an electrolyte salt for an electric double-layer capacitor. Examples of preferred lithium salts include $LiPF_6$, $LiBF_4$, $LiAsF_6$, $LiSbF_6$, and $LiN(SO_2C_2H_5)_2$.

A magnesium salt may also be used for further improving the capacity. Examples of preferred magnesium salts include $Mg(ClO_4)_2$ and $Mg(OOC_2H_5)_2$.

In the case where the electrolyte salt is the ammonium salt, the concentration is preferably 0.5 mol/L or higher. If the concentration is lower than 0.5 mol/L, the low-temperature characteristics will be poor and the initial internal resistance will be high. The electrolyte salt preferably has a concentration of 0.7 mol/L or higher.

The upper limit of the concentration is preferably 3.0 mol/L or lower and more preferably 2.5 mol/L or lower, in terms of low-temperature characteristics.

In the case where the ammonium salt is triethyl methyl ammonium tetrafluoroborate ($TEMABF_4$), the concentration is preferably 0.9 to 2.0 mol/L for excellent low-temperature characteristics.

In addition, in the case where the ammonium salt is spirobipyrrolidinium tetrafluoroborate ($SBPBF_4$), the concentration is preferably 0.8 to 2.0 mol/L.

Preferably, the electrolyte solution of the present invention further contains a polyethylene oxide having a weight average molecular weight of 2000 to 4000 and having —OH, —OCOOH, or —COOH at its end.

The addition of such a compound improves the stability of the electrode interface and the battery characteristics.

Examples of the polyethylene oxide include polyethylene oxide monool, polyethylene oxide carboxylic acid, polyethylene oxide dial, polyethylene oxide dicarboxylic acid, polyethylene oxide triol, and polyethylene oxide tricarboxylic acid. These may be used alone or in combination of two or more thereof.

Among these, a mixture of polyethylene oxide monool and polyethylene oxide dial, and a mixture of polyethylene oxide carboxylic acid and polyethylene oxide dicarboxylic acid are preferred, for better battery characteristics.

If the weight average molecular weight of the polyethylene oxide is too low, the resulting electrolyte solution may be prone to oxidative decomposition. The weight average molecular weight is more preferably 3000 to 4000.

The weight average molecular weight can be measured by gel permeation chromatography (GPC) versus polystyrene standards.

The polyethylene oxide content in the electrolyte solution is preferably $1 \times 10^{-6}$ to $1 \times 10^{-2}$ mol/kg. If the polyethylene oxide content is too high, the battery characteristics may be impaired.

The polyethylene oxide content is more preferably $5 \times 10^{-6}$ mol/kg or higher.

Preferably, the electrolyte solution of the present invention further contains, as an additive, at least one selected from the group consisting of unsaturated cyclic carbonates, fluorinated saturated cyclic carbonates, and cyclic sulfonic acid compounds. The addition of these compounds can suppress a decrease in battery characteristics.

The unsaturated cyclic carbonate is a cyclic carbonate having an unsaturated bond, i.e., a cyclic carbonate containing at least one carbon-carbon unsaturated bond in the molecule. Specific examples include vinylene carbonate compounds such as vinylene carbonate, methylvinylene carbonate, ethylvinylene carbonate, 4,5-dimethylvinylene carbonate, and 4,5-diethylvinylene carbonate; and vinylethylene carbonate compounds such as 4-vinylethylene carbonate (VEC), 4-methyl-4-vinylethylene carbonate, 4-ethyl-4-vinylethylene carbonate, 4-n-propyl-4-vinylene ethylene carbonate, 5-methyl-4-vinylethylene carbonate, 4,4-divinylethylene carbonate, 4,5-divinylethylene carbonate, 4,4-dimethyl-5-methylene ethylene carbonate, and 4,4-diethyl-5-methylene ethylene carbonate. Among these, vinylene carbonate, 4-vinylethylene carbonate, 4-methyl-4-vinylethylene carbonate, and 4,5-divinylethylene carbonate are preferred, and vinylene carbonate and 4-vinylethylene carbonate are particularly preferred.

The molecular weight of the unsaturated cyclic carbonate is not particularly limited, and it may be any value as long as the effects of the present invention are not significantly impaired. Preferably, the molecular weight is 50 or more, and 250 or less. In this range, the solubility of the unsaturated cyclic carbonate in the electrolyte solution can be easily ensured, and the effects of the present invention tend to be sufficiently achieved. The molecular weight of the unsaturated cyclic carbonate is more preferably 80 or more, and more preferably 150 or less.

In addition, a fluorinated unsaturated cyclic carbonate can also be suitably used as the unsaturated cyclic carbonate.

The number of fluorine atoms in the fluorinated unsaturated cyclic carbonate is not particularly limited as long as it is at least one. In particular, the number of fluorine atoms is usually 6 or less, preferably 4 or less, and most preferably 1 or 2.

Examples of fluorinated unsaturated cyclic carbonates include fluorinated vinylene carbonate derivatives, and fluorinated ethylene carbonate derivatives substituted by a substituent having an aromatic ring or a carbon-carbon double bond.

Examples of fluorinated vinylene carbonate derivatives include 4-fluorovinylene carbonate, 4-fluoro-5-methylvinylene carbonate, 4-fluoro-5-phenylvinylene carbonate, 4-allyl-5-fluorovinylene carbonate, and 4-fluoro-5-vinylvinylene carbonate.

Examples of fluorinated ethylene carbonate derivatives substituted by a substituent having an aromatic ring or a carbon-carbon double bond include 4-fluoro-4-vinylethylene carbonate, 4-fluoro-4-allylethylene carbonate, 4-fluoro-5-vinylethylene carbonate, 4-fluoro-5-allylethylene carbonate, 4,4-difluoro-4-vinylethylene carbonate, 4,4-difluoro-4-allylethylene carbonate, 4,5-difluoro-4-vinylethylene carbonate, 4,5-difluoro-4-allylethylene carbonate, 4-fluoro-4,5-divinylethylene carbonate, 4-fluoro-4,5-diallylethylene carbonate, 4,5-difluoro-4,5-divinylethylene carbonate, 4,5-difluoro-4,5-diallylethylene carbonate, 4-fluoro-4-phenylethylene carbonate, 4-fluoro-5-phenylethylene carbonate, 4,4-difluoro-5-phenylethylene carbonate, and 4,5-difluoro-4-phenylethylene carbonate.

The molecular weight of the fluorinated unsaturated cyclic carbonate is not particularly limited, and it may be any value as long as the effects of the present invention are not significantly impaired. Preferably, the molecular weight is 50 or more, and 500 or less. In this range, the solubility of the fluorinated unsaturated cyclic carbonate in the electrolyte solution can be easily ensured, and the effects of the present invention can be easily achieved.

The above unsaturated cyclic carbonates may be used alone or in any combination of two or more thereof at any ratio.

Examples of the fluorinated saturated cyclic carbonate include the compounds exemplified above as fluorinated saturated cyclic carbonates usable in the solvent.

Examples of the cyclic sulfonic acid compound include 1,3-propane sultone, 1,4-butane sultone, 1-fluoro-1,3-propane sultone, 2-fluoro-1,3-propane sultone, and 3-fluoro-1,3-propane sultone.

Among these, the electrolyte solution of the present invention preferably contains 1,3-propane sultone and/or 1,4-butane sultone, for improving high temperature characteristics.

In the case where the electrolyte solution contains, as an additive, at least one compound selected from the group consisting of the unsaturated cyclic carbonate, fluorinated saturated cyclic carbonate, and cyclic sulfonic acid compound, the content thereof in the electrolyte solution is preferably 0.1 to 10% by mass. More preferably, the content is 1% by mass or more and 5% by mass or less.

The electrolyte solution of the present invention may further contain any of other solvents or additives such as cyclic and chain carboxylic acid esters, ether compounds, nitrogen-containing compounds, boron-containing compounds, organosilicon-containing compounds, non-flammable (fire-retardant) agents, surfactants, high dielectric additives, cycle characteristics and rate characteristics improvers, and overcharge inhibitors, as long as the effects of the present invention are not impaired.

The cyclic carboxylic acid ester may be one having a total of 3 to 12 carbon atoms in the structural formula. Specific examples include gamma-butyrolactone, gamma-valerolactone, gamma-caprolactone, and isopsilon-caprolactone. Among these, gamma-butyrolactone is particularly preferred for improving battery characteristics associated with improved lithium ion dissociation.

Usually, the amount of cyclic carboxylic acid ester in 100% by mass of the solvent is preferably 0.1% by mass or more, and more preferably 1% by mass or more. In this range, the electrical conductivity of the electrolyte solution can be improved, and thus the large-current discharge characteristics of the electrolyte battery can be easily improved. In addition, the amount of cyclic carboxylic acid ester in the electrolyte solution is preferably 10% by mass or less, and more preferably 5% by mass or less. By setting an upper limit as described above, the viscosity of the electrolyte solution can be adjusted to a suitable range, a decrease in the electrical conductivity can be prevented, an increase in the resistance of the negative electrode can be suppressed, and the large-current discharge characteristics of the electrolyte battery can be easily adjusted to a suitable range.

In addition, a fluorinated cyclic carboxylic acid ester (a fluorine-containing lactone) can also be suitably used as the cyclic carboxylic acid ester. Examples of fluorine-containing lactones include a fluorine-containing lactone represented by the following formula (C):

[Chem. 39]

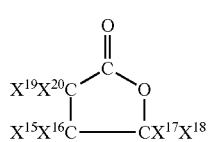

(C)

wherein $X^{15}$ to $X^{20}$ are the same or different, and each is —H, —F, —Cl, —CH$_3$, or a fluorinated alkyl group; provided that at least one of $X^{15}$ to $X^{20}$ is a fluorinated alkyl group.

Examples of fluorinated alkyl groups in $X^{15}$ to $X^{20}$ include —CFH$_2$, —CF$_2$H, —CF$_3$, —CH$_2$CF$_3$, —CF$_2$CF$_3$, —CH$_2$CF$_2$CF$_3$, and —CF(CF$_3$)$_2$. Among these, —CH$_2$CF$_3$ and —CH$_2$CF$_2$CF$_3$ are preferred for high oxidation resistance and for a safety improving effect.

If at least one of $X^{15}$ to $X^{20}$ is a fluorinated alkyl group, then, —H, —F, —Cl, —CH$_3$ or a fluorinated alkyl group may be substituted at only one or more positions of $X^{15}$ to $X^{20}$, preferably at 1 to 3 positions and more preferably at 1 to 2 positions, for good solubility of the electrolyte salt.

The substitution position of the fluorinated alkyl group is not particularly limited. Yet, for achieving good synthetic yield, $X^{17}$ and/or $X^{18}$, particularly $X^{17}$ or $X^{18}$, is preferably a fluorinated alkyl group, specifically, —CH$_2$CF$_3$ or —CH$_2$CF$_2$CF$_3$. $X^{15}$ to $X^{20}$ other than the fluorinated alkyl group are —H, —F, —Cl, or CH$_3$ individually, and —H is particularly preferred for good solubility of the electrolyte salt.

Examples of fluorine-containing lactones other than those represented by the above formula include a fluorine-containing lactone represented by the following formula (D)

[Chem. 40]

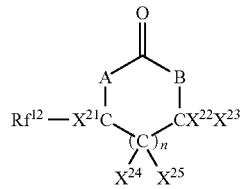

(D)

wherein one of A and B is CX$^{26}$X$^{27}$ (X$^{26}$ and X$^{27}$ are the same or different, and each is —H, —F, —Cl, —CF$_3$, —CH$_3$, or an alkylene group whose hydrogen atoms are optionally replaced by halogen atoms and which optionally contains a heteroatom in the chain), and the other is an oxygen atom; Rf$^{12}$ is a fluorinated alkyl group or fluorinated alkoxy group optionally having an ether bond; X$^{21}$ and X$^{22}$ are the same or different, and each is —H, —F, —Cl, —CF$_3$, or CH$_3$; X$^{23}$ to X$^{25}$ are the same or different, and each is —H, —F, —Cl, or an alkyl group whose hydrogen atoms are optionally replaced by halogen atoms and which optionally contains a heteroatom in the chain; and n is 0 or 1.

Examples of preferred fluorine-containing lactone represented by formula (D) include a five-membered ring structure represented by the following formula (E) for easy synthesis and good chemical stability:

[Chem. 41]

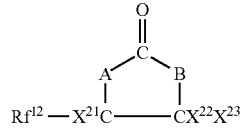

(E)

wherein A, B, Rf$^{12}$, X$^{21}$, X$^{22}$, and X$^{23}$ are as defined above for formula (D). Further, depending on a combination of A and B, examples also include a fluorine-containing lactone represented by the following formula (F):

[Chem. 42]

$$\text{Rf}^{12}-\text{X}^{21}\text{C}\underset{|}{\overset{|}{\phantom{X}}}\text{---}\text{CX}^{22}\text{X}^{23}\text{---O---C(=O)---CX}^{26}\text{X}^{27}$$ (F)

wherein $Rf^{12}$, $X^{21}$, $X^{22}$, $X^{23}$, $X^{26}$, and $X^{27}$ are as defined above for formula (D); and a fluorine-containing lactone represented by the following formula (G):

[Chem. 43]

(G)

wherein $Rf^{12}$, $X^{21}$, $X^{22}$, $X^{23}$, $X^{26}$, and $X^{27}$ are as defined for formula (D).

Among these, for example, the fluorine-containing lactones shown below improve the characteristics of the electrolyte solution of the present invention because they can particularly contribute to excellent characteristics such as high permittivity and high withstand voltage and provide good solubility of the electrolyte salt and low internal resistance:

[Chem. 44]

The addition of a fluorinated cyclic carboxylic acid ester provides effects of improving the ionic conductivity, safety, and stability at a high temperature.

Examples of the chain carboxylic acid ester may be one having a total of 3 to 7 carbon atoms in the structural formula. Specific examples include methyl acetate, ethyl acetate, n-propyl acetate, isopropyl acetate, n-butyl acetate, isobutyl acetate, t-butyl acetate, methyl propionate, ethyl propionate, n-propyl propionate, isopropyl propionate, n-butyl propionate, isobutyl propionate, t-butyl propionate, methyl butyrate, ethyl butyrate, n-propyl butyrate, n-propyl butyrate, isopropyl butyrate, methyl isobutyrate, ethyl isobutyrate, n-propyl isobutyrate, and isopropyl isobutyrate.

Among these, methyl acetate, ethyl acetate, n-propyl acetate, n-butyl acetate, methyl propionate, ethyl propionate, n-propyl propionate, isopropyl propionate, methyl butyrate, and ethyl butyrate are preferred for improving the ionic conductivity due to low viscosity.

In addition, a fluorinated chain carboxylic acid ester can also be suitably used. As a fluorine-containing ester, a fluorinated chain carboxylic acid ester represented by the following formula (H) is preferred for high flame retardancy, good compatibility with other solvents, and good oxidation resistance:

$$Rf^{10}COORf^{11}$$ (H)

wherein $Rf^{10}$ is a C1-C2 fluorinated alkyl group, and $Rf^{11}$ is a C1-C4 fluorinated alkyl group.

Examples of $Rf^{10}$ include $CF_3$—, $CF_3CF_2$—, $HCF_2CF_2$—, $HCF_2$—, $CH_3CF_2$—, and $CF_3CH_2$—. Among these, $CF_3$— and $CF_3CF_2$— are particularly preferred for good rate characteristics.

Examples of $Rf^{11}$ include $CF_3$, —$CF_2CF_3$, —$CH(CF_3)_2$, —$CH_2CF_3$, —$CH_2CH_2CF_3$, —$CH_2CF_2CFHCF_3$, —$CH_2C_2F_5$, —$CH_2CF_2CF_2H$, —$CH_2CH_2C_2F_5$, —$CH_2CF_2CF_3$, and —$CH_2CF_2CF_2CF_3$. Among these, —$CH_2CF_3$, —$CH(CF_3)_2$, —$CH_2C_2F_5$, and —$CH_2CF_2CF_2H$ are particularly preferred for good compatibility with other solvents.

Specific examples of fluorinated chain carboxylic acid esters include one or two or more kinds of $CF_3C(=O)OCH_2CF_3$, $CF_3C(=O)OCH_2CH_2CF_3$, $CF_3C(=O)OCH_2C_2F_5$, $CF_3C(=O)OCH_2CF_2CF_2H$, and $CF_3C(=O)OCH(CF_3)_2$. Among these, $CF_3C(=O)OCH_2C_2F_5$, $CF_3C(=O)OCH_2CF_2CF_2H$, $CF_3C(=O)$ $OCH_2CF_3$, and $CF_3C(=O)OCH(CF_3)_2$ are particularly preferred for good compatibility with other solvents and good rate characteristics.

The ether compound is preferably a C3-C10 chain ether or a C3-C6 cyclic ether.

Examples of C3-C10 chain ethers include diethyl ether, di-n-butyl ether, dimethoxymethane, methoxyethoxymethane, diethoxymethane, dimethoxyethane, methoxyethoxyethane, diethoxyethane, ethylene glycol di-n-propyl ether, ethylene glycol di-n-butyl ether, and diethylene glycol dimethyl ether.

In addition, a fluorinated ether can also be suitably used as the ether compound.

Examples of the fluorinated ether include a fluorinated ether (I) represented by the following formula (I):

$$Rf^1\text{---O---}Rf^2$$ (I)

wherein $Rf^1$ and $Rf^2$ are the same or different, and each is a C1-C10 alkyl group or a C1-C10 fluorinated alkyl group; provided that at least one of $Rf^1$ and $Rf^2$ is a fluorinated alkyl group. The addition of the fluorinated ether (I) improves the flame retardancy of the electrolyte solution as well as the stability and safety thereof at a high temperature and a high voltage.

In the above formula (I), it suffices as long as at least one of $Rf^1$ and $Rf^2$ is a C1-C10 fluorinated alkyl group. Yet, for further improving the flame retardancy of the electrolyte solution as well as the stability and safety thereof at a high temperature and a high voltage, it is preferred that both of $Rf^1$ and $Rf^2$ be C1-C10 fluorinated alkyl groups. In this case, $Rf^1$ and $Rf^2$ may be the same or different from each other.

In particular, it is preferred that $Rf^1$ and $Rf^2$ be the same or different, $Rf^1$ be a C3-C6 fluorinated alkyl group, and $Rf^2$ be a C2-C6 fluorinated alkyl group.

If the total carbon number of $Rf^1$ and $Rf^2$ is too small, the boiling point of the fluorinated ether will be too low. If the carbon number of $Rf^1$ or $Rf^2$ is too large, the solubility of the electrolyte salt will decrease, adversely affecting the compatibility with other solvents and increasing the viscosity. As a result, the rate characteristics (viscosity) will decrease. Advantageously, the carbon number of $Rf^1$ is 3 or 4 and the carbon number of $Rf^2$ is 2 or 3, for a high boiling point and excellent rate characteristics.

The fluorinated ether (I) preferably has a fluorine content of 40 to 75% by mass. The fluorine content in the above range can result in an electrolyte solution that is particularly excellent in the balance between non-flammability and compatibility. The fluorine content in the above range is also preferred for good oxidation resistance and safety.

The lower limit of the fluorine content is more preferably 45% by mass, still more preferably 50% by mass, and particularly preferably 55% by mass. The upper limit is more preferably 70% by mass, and still more preferably 66% by mass.

The fluorine content in the fluorinated ether (I) is a value calculated based on the structural formula of the fluorinated ether (I) using the following formula: {(Number of fluorine atoms×19)/Molecular weight of the fluorinated ether (I)}× 100(%).

Examples of $Rf^1$ include $CF_3CF_2CH_2-$, $CF_3CFHCF_2-$, $HCF_2CF_2CF_2-$, $HCF_2CF_2CH_2-$, $CF_3CF_2CH_2CH_2-$, $CF_3CFHCF_2CH_2-$, $HCF_2CF_2CF_2CF_2-$, $HCF_2CF_2CF_2CH_2-$, $HCF_2CF_2CH_2CH_2-$, and $HCF_2CF(CF_3)CH_2-$. Examples of $Rf^2$ include $-CH_2CF_2CF_3$, $-CF_2CFHCF_3$, $-CF_2CF_2CF_2H$, $-CH_2CF_2CF_2H$, $-CH_2CH_2CF_2CF_3$, $-CH_2CF_2CFHCF_3$, $-CF_2CF_2CF_2CF_2H$, $-CH_2CF_2CF_2CF_2H$, $-CH_2CH_2CF_2CF_2H$, $-CH_2CF(CF_3)CF_2H$, $-CF_2CF_2H$, $-CH_2CF_2H$, and $-CF_2CH_3$.

Specific examples of the fluorinated ether (I) include $HCF_2CF_2CH_2OCF_2CF_2H$, $CF_3CF_2CH_2OCF_2CF_2H$, $HCF_2CF_2CH_2OCF_2CFHCF_3$, $CF_3CF_2CH_2OCF_2CFHCF_3$, $C_6F_{13}OCH_3$, $C_6F_{13}OC_2H_5$, $C_8F_{17}OCH_3$, $C_8F_{17}OC_2H_5$, $CF_3CFHCF_2CH(CH_3)OCF_2CFHCF_3$, $HCF_2CF_2OCH(C_2H_5)_2$, $HCF_2CF_2OC_4H_9$, $HCF_2CF_2OCH_2CH(C_2H_5)_2$, and $HCF_2CF_2OCH_2CH(CH_3)_2$.

Among these, the fluorinated ether (I) having $HCF_2-$ or $CF_3CFH-$ at one end or both ends has excellent polarization characteristics and a high boiling point. The boiling point of the fluorinated ether (I) is preferably 67 to 120° C. The boiling point is more preferably 80° C. or higher, and still more preferably 90° C. or higher.

Examples of the above fluorinated ether (I) include one or two or more kinds of $CF_3CH_2OCF_2CFHCF_3$, $CF_3CF_2CH_2OCF_2CFHCF_3$, $HCF_2CF_2CH_2OCF_2CFHCF_3$, $HCF_2CF_2CH_2OCH_2CF_2CF_2H$, $CF_3CFHCF_2CH_2OCF_2CFHCF_3$, $HCF_2CF_2CH_2OCF_2CF_2H$, and $CF_3CF_2CH_2OCF_2CF_2H$.

Among these, at least one selected from the group consisting of $HCF_2CF_2CH_2OCF_2CFHCF_3$ (boiling point of 106° C.), $CF_3CF_2CH_2OCF_2CFHCF_3$ (boiling point of 82° C.), $HCF_2CF_2CH_2OCF_2CF_2H$ (boiling point of 92° C.), and $CF_3CF_2CH_2OCF_2CF_2H$ (boiling point of 68° C.) is preferred because it is advantageous in providing a high boiling point and good compatibility with other solvents as well as good solubility of the electrolyte salt. At least one selected from the group consisting of $HCF_2CF_2CH_2OCF_2CFHCF_3$ (boiling point of 106° C.) and $HCF_2CF_2CH_2OCF_2CF_2H$ (boiling point of 92° C.) is more preferred.

Examples of O3-C6 cyclic ethers include 1,3-dioxane, 2-methyl-1,3-dioxane, 4-methyl-1,3-dioxane, 1,4-dioxane, and fluorinated compounds of these ethers. Among these, dimethoxymethane, diethoxymethane, ethoxymethoxymethane, ethylene glycol-n-propylether, ethylene glycol di-n-butylether, and diethylene glycol dimethylether are preferred because they have higher solvation ability to lithium ions and improve ionic dissociation. Dimethoxymethane, diethoxymethane, and ethoxymethoxymethane are particularly preferred for providing low viscosity and high ionic conductivity.

Examples of the nitrogen-containing compound include nitrile, fluorine-containing nitrile, carboxylic acid amide, fluorine-containing carboxylic acid amide, sulfonic acid amide, and fluorine-containing sulfonic acid amide. In addition, 1-methyl-2-pyrrolidinone, 1-methyl-2-piperidone, 3-methyl-2-oxazilidinone, 1,3-dimethyl-2-imidazolidinone, and N-methylsuccinimide can also be used.

Examples of the boron-containing compound include borate (such as trimethyl borate and triethyl borate), ether borate, and alkyl borate.

Examples of the organic silicon-containing compound include $(CH_3)_4-Si$ and $(CH_3)_3-Si-Si(CH_3)_3$.

Examples of the non-flammable (fire-retardant) agents include phosphate esters and phosphazene-based compounds. Examples of the phosphate ester include fluorine-containing alkyl phosphate esters, non-fluorinated alkyl phosphate esters, and aryl phosphate esters. Among these, fluorine-containing alkyl phosphate esters are preferred because non-flammability can be achieved with a small amount thereof.

Specific examples of the fluorine-containing alkyl phosphate esters include a fluorine-containing dialkyl phosphate ester disclosed in JP-A H11-233141 as well as a cyclic alkyl phosphate ester and a fluorine-containing trialkyl phosphate ester disclosed in JP-A H11-283669.

The non-flammable (fire-retardant) agent is preferably $(CH_3O)_3P=O$, $(CF_3CH_2O)_3P=O$, or the like.

The surfactant may be any of cationic, anionic, non-ionic, and ampholytic surfactants. Yet, for good cycle characteristics and rate characteristics, a fluorine-containing surfactant is preferred.

Examples of preferred fluorine-containing surfactants include a fluorine-containing carboxylate represented by the following formula (3):

$$Rf^1COO^-M^+ \quad (3)$$

wherein $Rf^1$ is a C3-C10 fluorine-containing alkyl group optionally having an ether bond; and $M^+$ is $Li^+$, $Na^+$, $K^+$, or $NHR'_3^+$ (each R' is the same or different, and represents H or a C1-C3 alkyl group); and fluorine-containing sulfonate represented by the following formula (4):

$$Rf^2SO_3^-M^+ \quad (4)$$

wherein $Rf^2$ is a C3-C10 fluorine-containing alkyl group optionally having an ether bond; and $M^+$ is $Li^+$, $Na^+$, $K^+$, or $NHR'_3^+$ (each R' is the same or different, and represents H or a C1-C3 alkyl group).

The amount of the surfactant in the electrolyte solution is preferably 0.01 to 2% by mass for reducing the surface tension of the electrolyte solution without decreasing the charge-discharge cycle characteristics.

Examples of the high dielectric additives include sulfolane, methylsulfolane, γ-butyrolactone, γ-valerolactone, acetonitrile, and propionitrile.

Examples of the cycle characteristics and rate characteristics improvers include methyl acetate, ethyl acetate, tetrahydrofuran, and 1,4-dioxane.

The overcharge inhibitor is preferably one having an aromatic ring for inhibiting explosion or fire of the battery in the case of overcharge or the like. Examples of the overcharge inhibitor having an aroma ring include aromatic compounds such as cyclohexylbenzene, biphenyl, alkylbiphenyl, terphenyl, partial hydrides of terphenyl, t-butylbenzene, t-amylbenzene, diphenyl ether, benzofulan, dibenzofulan, dichloroaniline, and toluene; fluorinated aromatic compounds such as hexafluorobenzene, fluorobenzene, 2-fluorobiphenyl, o-cyclohexyl fluorobenzene, and p-cyclohexyl fluorobenzene; and fluorine-containing anisole compounds such as 2,4-difluoroanisole, 2,5-difluoroanisole, 2,6-difluoroanisole, and 3,5-difluoroanisole, Among these, aromatic compounds such as biphenyl, alkyl biphenyl, terphenyl, partial hydrides of terphenyl, cyclohexylbenzene, t-butylbenzene, t-amylbenzene, diphenyl ether, and dibenzofulan are preferred. These may be used alone or in combination of two or more thereof. In the case of a combination of two or more thereof, in particular, the following combinations are preferred in terms of the balance between overcharge prevention characteristics and high-temperature storage characteristics: a combination of cyclohexylbenzene with t-butylbenzene or t-amylbenzene; and a combination of at least one selected from oxygen-free aromatic compounds such as biphenyl, alkyl biphenyl, terphenyl, a partial hydride of terphenyl, cyclohexylbenzene, t-butylbenzene, and t-amylbenzene, with at least one selected from oxygen-containing aromatic compounds such as diphenyl ether and dibenzofulan.

The amount of the overcharge inhibitor in the electrolyte solution is preferably 0.1 to 5% by mass for preventing explosion or fire of the battery in the case of overcharge or the like.

The electrolyte solution of the present invention may further contain other publicly known auxiliary agents as long as the effects of the present invention are not impaired. Examples of the other publicly known auxiliary agent include carbonate compound such as erythritan carbonate, Spiro bis-dimethylene carbonate, and methoxyethyl-methyl carbonate; carboxylic anhydrides such as succinic anhydride, glutaric anhydride, maleic anhydride, citraconic anhydride, glutaconic anhydride, itaconic anhydride, diglycolic anhydride, cyclohexane dicarboxylic anhydride, cyclopentanetetracarboxylic dianhydride, and phenyl succinic anhydride; Spiro compounds such as 2,4,8,10-tetraoxaspiro[5,5]undecane, and 3,9-divinyl-2,4,8,10-tetraoxaspiro[5,5]undecane; sulfur-containing compounds such as ethylene sulfite, methyl fluorosulfonate, ethyl fluorosulfonate, methyl methanesulfonate, ethyl methanesulfonate, busulfan, sulfolene, diphenyl sulfone, N,N-dimethyl methane sulfone amide, N,N-diethyl methane sulfone amide, and like other chain sulfones, fluorine-containing chain sulfone, chain sulfonate, fluorine-containing chain sulfonate, cyclic sulfones, fluorine-containing cyclic sulfone, halides of sulfonic acid, and halides of fluorine-containing sulfonic acid; and fluorine-containing aromatic compounds such as heptane, octane, nonane, decane, cycloheptane, and other like hydrocarbon compounds. These may be used alone or in combination of two or more thereof. The addition of these auxiliary agents can improve capacity maintaining characteristics and cycle characteristics after high-temperature storage.

The electrolyte solution of the present invention may also be formed into an electrolyte gel in a gel-like (plasticized) form by further adding a polymeric material to the electrolyte solution.

Examples of polymeric materials include conventionally known polyethylene oxide, polypropylene oxide, and modified forms thereof (JP-A H08-222270 and JP-A 2002-100405); fluororesins such as polyacrylic polymers, polyacrylonitrile, polyvinylidene fluoride, and vinylidene fluoride-hexafluoropropylene copolymers (JP-T H04-506726, JP-T H08-507407, and JP-A H10-294131); and composites of these fluororesins and hydrocarbon resins (JP-A H11-35765 and JP-A H11-86630). In particular, polyvinylidene fluoride and vinylidene fluoride-hexafluoropropylene copolymers are desirably used as polymeric materials for gel electrolytes.

In addition, the electrolyte solution of the present invention may also contain anion-conductive compound disclosed in Japanese Patent Application No. 2004-301934.

The ion-conductive compound is an amorphous fluorine-containing polyether compound having a fluorine-containing group at a side chain, represented by formula (1-1):

$$A\text{-}(D)\text{-}B \qquad (1\text{-}1)$$

wherein D represents formula (2-1):

$$\text{-}(D1)_n\text{-}(FAE)_m\text{-}(AE)_p\text{-}(Y)_q\text{—} \qquad (2\text{-}1)$$

wherein D1 is an ether unit having a fluorine-containing ether group at a side chain, represented by formula (2a):

[Chem. 45]

wherein Rf is a fluorine-containing ether group optionally having a crosslinking functional group; and $R^{10}$ is a group or bonding site for binding Rf and the main chain;

FAE is an ether unit having a fluorinated alkyl group at a side chain, represented by formula (2b):

[Chem. 46]

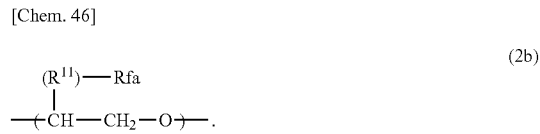

wherein Rfa is a hydrogen atom or a fluorinated alkyl group optionally having a crosslinking functional group; and $R^{11}$ is a group or bonding site for binding Rfa and the main chain;

AE is an ether unit represented by formula (2c):

[Chem. 47]

wherein $R^{13}$ is a hydrogen atom, an alkyl group optionally having a crosslinking functional group, an aliphatic cyclic hydrocarbon group optionally having a crosslinking functional group, or an aromatic hydrocarbon optionally having a crosslinking functional group; and $R^{12}$ is a group or a bonding site for binding $R^{13}$ and the main chain;

Y is a unit having at least one of formulae (2d-1) to (2d-3):

[Chem. 48]

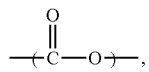
(2d-1)

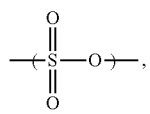
(2d-2)

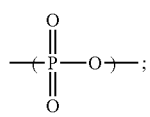
(2d-3)

n is an integer of 0 to 200; m is an integer of 0 to 200; p is an integer of 0 to 10000; and q is an integer of 1 to 100; provided that n+m is not 0, and the bond order of D1, FAE, AE, and Y is not specified;

A and B are the same or different, and each is a hydrogen atom, an alkyl group optionally having a fluorine atom and/or a crosslinking functional group, a phenyl group optionally having a fluorine atom and/or a crosslinking functional group, a —COOH group, —OR (wherein R is a hydrogen atom or an alkyl group optionally having a fluorine atom and/or a crosslinking functional group), an ester group, or a carbonate group (a —COOH group, —OR, an ester group, and a carbonate group are excluded in the case where D is terminated by an oxygen atom).

The electrolyte solution of the present invention may further contain other additives as needed. Examples of the other additives include metal oxide and glass.

The electrolyte solution of the present invention preferably contains 0.5 to 70 ppm of HF. The addition of HF can promote film formation by the additives. If the HF content is too low, the ability of the additives to form a film at the negative electrode will decrease, which tends to decrease the battery characteristics. If the HF content is too high, the oxidation resistance of the electrolyte solution tends to decrease due to HF. In the case of the electrolyte solution of the present invention, the HF content in the above range will not decrease the recovery capacity ratio of the battery after high-temperature storage. HF in the electrolyte solution of the present invention can include a derivative of the fluorine-containing compound (A) or the fluorine-containing compound (B).

The HF content is more preferably 1 ppm or more, and still more preferably 2.5 ppm or more. The HF content is also more preferably 60 ppm or less, still more preferably 50 ppm or less, and particularly preferably 30 ppm or less.

The HF content can be measured by the neutralization titration method.

An example of the electrolyte solution of the present invention is an electrolyte solution, wherein the mass ratio of the total of non-fluorinated or fluorinated saturated cyclic carbonates and non-fluorinated chain carbonates to the total of fluorine-containing compound (A) and fluorine-containing compound (B) in the solvent (i.e., (non-fluorinated or fluorinated saturated cyclic carbonates+non-fluorinated chain carbonates)/(A+B)) is 89.99/10.01 or less, and the HF content in the electrolyte solution is 0.5 to 70 ppm. The upper limit of the mass ratio is preferably 85/15, and more preferably 80/20. The lower limit of the mass ratio is preferably 25/75, and more preferably 30/70. A more preferred range of the HF content is as described above.

The electrolyte solution of the present invention may be prepared by any method, using the above components.

As described above, the electrolyte solution of the present invention contains a specific fluorine-containing compound. Thus, a battery having excellent high-temperature storage characteristics can be produced using the electrolyte solution of the present invention. The electrolyte solution of the present invention is suitably applicable to, for example, electrochemical devices such as lithium-ion secondary batteries and electric double-layer capacitors. Another aspect of the present invention is an electrochemical device containing the electrolyte solution.

Examples of electrochemical devices include lithium-ion secondary batteries, capacitors (electric double-layer capacitors), radical batteries, solar cells (particularly, dye sensitized solar cells), fuel cells, various electrochemical sensors, electrochromic devices, electrochemical switching devices, aluminium electrolytic capacitors, and tantalum electrolytic capacitors. Among these, lithium-ion secondary batteries and electric double-layer capacitors are preferred.

A lithium-ion secondary battery is described below as an example of an electrochemical device containing the electrolyte solution of the present invention. Still another aspect of the present invention is a lithium-ion secondary battery containing the electrolyte solution of the present invention.

The lithium-ion secondary battery of the present invention includes a positive electrode, a negative electrode, and the above-described electrolyte solution.

<Positive Electrode>

The positive electrode includes a positive electrode mixture containing a positive electrode active material (i.e., a material of a positive electrode), and a current collector.

Any positive electrode active material can be used as long as it can electrochemically store and release lithium ions. For example, a material containing lithium and at least one transition metal is preferred. Specific examples include a lithium-containing transition metal composite oxide and a lithium-containing transition metal phosphate compound. Among these, the positive electrode active material is particularly preferably a lithium-containing transition metal composite oxide that generates high voltage.

Examples of the lithium-containing transition metal composite oxide include, a lithium-manganese spinal composite oxide represented by formula (5): $Li_aMn_{2-b}M^1{}_bO_4$ wherein $0.9 \leq a$; $0 \leq b \leq 1.5$; and $M^1$ is at least one metal selected from the group consisting of Fe, Co, Ni, Cu, Zn, Al, Sn, Cr, V, Ti, Mg, Ca, Sr, B, Ga, In, Si, and Ge;

a lithium-nickel composite oxide represented by formula (6) $LiNi_{1-c}M^2{}_cO_2$ wherein $0 \leq c \leq 0.5$; and $M^2$ is at least one metal selected from the group consisting of Fe, Co, Mn, Cu, Zn, Al, Sn, Cr, V, Ti, Mg, Ca, Sr, B, Ga, In, Si, and Ge; and a lithium-cobalt composite oxide represented by formula (7): $LiCo_{1-d}M^3{}_dO_2$ wherein $0 \leq d \leq 0.5$; and $M^3$ is at least one metal selected from the group consisting of Fe, Ni, Mn, Cu, Zn, Al, Sn, Cr, V, Ti, Mg, Ca, Sr, B, Ga, In, Si, and Ge.

Among these, $LiCoO_2$, $LiMnO_2$, $LiNiO_2$, $LiMn_2O_4$, $LiNi_{0.8}Co_{0.15}Al_{0.05}O_2$, and $LiNi_{1/3}Co_{1/3}Mn_{1/3}O_2$ are preferred for providing a lithium-ion secondary battery having high energy density and high output.

Other examples of the positive electrode active material include $LiFePO_4$, $LiNi_{0.8}Co_{0.2}O_2$, $Li_{1.2}Fe_{0.4}Mn_{0.4}O_2$, $LiNi_{0.5}Mn_{0.5}O_2$, and $LiV_3O_6$.

In addition, the addition of lithium phosphate to the positive electrode active material is preferred because it improves continuous charge characteristics. The use of lithium phosphate is not limited. Yet, it is preferred to mix the positive electrode active material with lithium phosphate. The lower limit of the amount of lithium phosphate to be used relative to the total amount of the positive electrode active material and the lithium phosphate is preferably 0.1% by mass or more, more preferably 0.3% by mass or more, and still more preferably 0.5% by mass or more; and the upper limit thereof is preferably 10% by mass or less, more preferably 8% by mass or less, and still more preferably 5% by mass or less.

In addition, the positive electrode active material in which a material having a different composition is attached to the surface thereof may be used. Examples of surface-attached materials include oxides such as aluminium oxide, silicon oxide, titanium oxide, zirconium oxide, magnesium oxide, calcium oxide, boron oxide, antimony oxide, and bismuth oxide; sulfates such as lithium sulfate, sodium sulfate, potassium sulfate, magnesium sulfate, calcium sulfate, and aluminum sulfate; carbonates such as lithium carbonate, calcium carbonate, and magnesium carbonate; and carbon.

These surface-attached materials can be attached to the surface of the positive electrode active material by the following methods, for example: a method in which a surface-attached material is dissolved or suspended in a solvent and attached to the positive electrode active material by impregnation, followed by drying; a method in which a precursor of a surface-attached material is dissolved or suspended in a solvent and attached to the positive electrode active material by impregnation, followed by reaction under heat or the like; and a method in which a surface-attached material is attached to a precursor of the positive electrode active material and fired at the same time. In the case of attaching carbon, it can be done by a method of mechanically attaching carbonaceous substance at a later time in the form of activated carbon, for example.

The lower limit of the amount of surface-attached material in mass relative to the positive electrode active material is preferably 0.1 ppm or more, more preferably 1 ppm or more, and still more preferably 10 ppm or more; and the upper limit of the amount thereof is preferably 20% or less, more preferably 10% or less, and still more preferably 5% or less. The surface-attached material can suppress an oxidation reaction of the electrolyte solution on the surface of the positive electrode active material, and can improve the battery life. If the attached amount is too small, its effect will be insufficient, whereas if the attached amount is too large, it will impede the movement of lithium ions, which may result in increased resistance.

Examples of the shape of particles of the positive electrode active material include conventional shapes such as lump, polyhedron, sphere, oval sphere, plate, needle, and pillar. Primary particles may aggregate and form secondary particles.

The tap density of the positive electrode active material is preferably 0.5 g/cm$^3$ or more, more preferably 0.8 g/cm$^3$ or more, and still more preferably 1.0 g/cm$^3$ or more. If the tap density of the positive electrode active material is less than the lower limit, formation of a positive electrode active material layer will require larger amounts of dispersion medium, conducting material, and binding agent, thus limiting the filling rate of the positive electrode active material into the positive electrode active material layer. As a result, the battery capacity may be limited. With the use of a composite oxide powder having high tap density, a positive electrode active material layer having high density can be formed. In general, it is better if the tap density is higher. The upper limit is not particularly limited, yet, if the tap density is too high, the diffusion rate of lithium ions in the electrolyte solution as a medium in the positive electrode active material layer will be controlled, which may decrease load characteristics. Thus, the upper limit is preferably 4.0 g/cm$^3$ or lower, more preferably 3.7 g/cm$^3$ or lower, and still more preferably 3.5 g/cm$^3$ or lower. In the present invention, the tap density is determined as the density (g/cc) of the filled powder (i.e., tap density), as measured by introducing 5 to 10 g of the positive electrode active material powder into a 10-ml glass graduated cylinder and tapping the graduated cylinder 200 times at a stroke of about 20 mm.

The median size d50 of particles of the positive electrode active material (or the secondary particle size in the case where the primary particles have aggregated and formed the secondary particles) is preferably 0.3 μm or more, more preferably 0.5 μm or more, still more preferably 0.8 μm or more, and most preferably 1.0 μm or more; at the same time, it is preferably 30 μm or less, more preferably 27 μm or less, still more preferably 25 μm or less, and most preferably 22 μm or less. If the median size is lower than the above lower limit, the resulting product may not have high tap density. If the median size is above the upper limit, lithium in the particles takes time to diffuse. This may cause a decrease in battery performance and other problems. For example, when forming a battery positive electrode (i.e., when making components such as an active material, a conducting material, and a binder into slurry with a solvent, and applying the obtained slurry in the form of a thin film), streaks may be formed on the film. Herein, mixing two or more types of the positive electrode active materials having different median sizes d50 can further improve filling performance during formation of the positive electrode.

In the present invention, the median size d50 is measured by a publicly known laser diffraction scattering particle size distribution analyzer. In the case of using a particle size distribution meter "LA-920" available from HORIBA, measurement is performed by using 0.1% by mass of a sodium hexametaphosphate aqueous solution as a dispersion medium. First, ultrasonic dispersion is performed for 5 minutes, and then the refractive index is set to 1.24 for measurement.

In the case where the secondary particles are formed by aggregation of the primary particles, the average primary particle size of the positive electrode active material is preferably 0.05 μm or more, more preferably 0.1 μm or more, and still more preferably 0.2 μm or more; and the upper limit is preferably 5 μm or less, more preferably 4 μm or less, still more preferably 3 μm or less, and most preferably 2 μm or less. If the average primary particle size is above the upper limit, it will be difficult to form the secondary particles in the spherical shape. This adversely affects powder filling performance and greatly decreases the specific surface area. As a result, the battery performance such as output characteristics may be very likely to decrease. Conversely, if the average primary particle size is less than the lower limit, problems such as poor charge-discharge reversibility may occur because crystals are usually underdeveloped in that case.

In the present invention, the primary particle size is measured by observation with a scanning electron microscope (SEM). Specifically, the longest segment of the boundary of each primary particle in the horizontal direction along the horizontal straight lines in an image at 10000 times magnification is determined for any 50 primary particles, and the average value is determined as the primary particle size.

The BET specific surface area of the positive electrode active material is preferably 0.1 $m^2/g$ or more, more preferably 0.2 $m^2/g$ or more, and still preferably 0.3 $m^2/g$ or more. The upper limit thereof is preferably 50 $m^2/g$ or less, more preferably 40 $m^2/g$ or less, and still preferably 30 $m^2/g$ or less. If the BET specific surface area is less than the above range, the battery performance tends to decrease. Conversely, if it is more than the above range, it will be difficult to increase the tap density, and the coating properties may be easily impaired during formation of the positive electrode active material layer.

In the present invention, the BET specific surface area is a value measured with a specific surface area meter (for example, a fully automatic specific surface area meter available from Ohkura Riken Co. Ltd.) in the following manner. First, samples are pre-dried at 150° C. for 30 minutes under nitrogen flow. Subsequently, the BET specific surface area is measured by the nitrogen-adsorption BET single-point method using the flowing gas method with a nitrogen-helium gas mixture that has been precisely adjusted such that the pressure of the nitrogen relative to the atmospheric pressure is 0.3.

The lithium-ion secondary battery of the present invention must have high output when used as a large lithium-ion secondary battery for hybrid vehicles and for dispersed power sources. Thus, it is preferred that the secondary particles be the main particles of the positive electrode active material.

The particles of the positive electrode active material preferably include 0.5 to 7.0% by volume of fine particles having an average secondary particle size of 40 µm or less and an average primary particle size of 1 µm or less. The presence of the fine particles having an average primary particle size of 1 µm or less contributes to an increase in the contact area with the electrolyte solution as well as an increase in the rate of diffusion of lithium ions between the electrodes and the electrolyte solution. As a result, the output performance of the battery can be improved.

As a method for producing a positive electrode active material, a method commonly used to produce an inorganic compound is used. Spherical and oval spherical active materials, in particular, can be produced by various methods. For example, a transition metal raw material is dissolved or dispersed by grinding in a solvent such as water; the pH is adjusted under stirring to prepare and collect a spherical precursor, which is then dried as needed; and subsequently, Li sources such as LiOH, $Li_2CO_3$, and $LiNO_3$ are added to the precursor, followed by firing at a high temperature, whereby an active material is obtained.

To produce a positive electrode, the above-listed examples of the positive electrode active materials may be used alone or in any combination of one or more thereof having different compositions at any ratio. In this case, examples of preferred combinations include a combination of $LiCoO_2$ with $LiMn_2O_4$ or the material where a part of Mn is replaced by another transition metal or the like (for example, $LiNi_{0.33}Co_{0.33}Mn_{0.33}O_2$), or a combination with $LiCoO_2$ or the material where a part of Co is replaced by another transition metal or the like.

The positive electrode active material content is preferably 50 to 99% by mass and more preferably 80 to 99% by mass of the positive electrode mixture, for high battery capacity. The positive electrode active material content in the positive electrode active material layer is preferably 80% by mass or more, more preferably 82% by mass or more, and particularly preferably 84% by mass or more. The upper limit is preferably 99% by mass or less, and more preferably 98% by mass or less. If the positive electrode active material content in the positive electrode active material layer is low, the electrical capacity may be insufficient. Conversely, if the content is too high, the strength of the positive electrode may be insufficient.

The positive electrode mixture preferably further contains a binding agent, a thickener, and a conducting material.

Any binding agent can be used as long as it is a material that is safe to use in a solvent and an electrolyte solution to be used for producing an electrode. Examples include polyvinylidene fluoride, polytetrafluoroethylene, polyethylene, polypropylene, SBR (styrene-butadiene rubber), isoprene rubber, butadiene rubber, ethylene-acrylic acid copolymers, ethylene-methacrylic acid copolymers, polyethylene terephthalate, polymethyl methacrylate, polyimide, aromatic polyimide, cellulose, nitrocellulose, NBR (acrylonitrile-butadiene rubber), fluororubber, ethylene-propylene rubber, styrene-butadiene-styrene block copolymers or hydrogen additives thereof, EPDM (ethylene-propylene-diene terpolymer), styrene-ethylene-butadiene-ethylene copolymers, styrene-isoprene-styrene block copolymers or hydrogen additives thereof, syndiotactic-1,2-polybutadiene, polyvinyl acetate, ethylene-vinyl acetate copolymers, propylene-α-olefin copolymers, fluorinated polyvinylidene fluoride, polytetrafluoroethylene-ethylene copolymers, and polymeric compositions having ionic conductivity of alkali metal ions (particularly, lithium ions). These materials may be used alone or in any combination of two or more thereof at any ratio.

The binding agent content (percentage) in the positive electrode active material layer is usually 0.1% by mass or higher, preferably 1% by mass or higher, and still more preferably 1.5% by mass or higher. At the same time, it is usually 80% by mass or lower, preferably 60% by mass or lower, more preferably 40% by mass or lower, and most preferably 10% by mass or lower. If the percentage of the binding agent is too low, the mechanical strength of the positive electrode may be insufficient because the positive electrode active material cannot be sufficiently held, and the battery performance such as cycle characteristics may be poor. On the other hand, if the percentage is too high, the battery capacity and conductivity may decrease.

Examples of the thickener include carboxymethylcellulose, methylcellulose, hydroxymethylcellulose, ethylcellulose, polyvinyl alcohol, oxidized starch, phosphorylated starch, casein, and their salts. These may be used alone or in any combination of two or more thereof at any ratio.

The percentage of the thickener relative to the active material is usually 0.1% by mass or higher, preferably 0.2% by mass or higher, and more preferably 0.3% by mass or higher. At the same time, it is usually 5% by mass or lower, preferably 3% by mass or lower, and more preferably 2% by mass or lower. If the percentage is less than the above range, the coating properties may markedly decrease. If the percentage is more than the above range, the percentage of the active material in the positive electrode active material layer will decrease, which may cause problems such as a decrease in the battery capacity and an increase in the resistance between positive electrode active materials.

As the conducting material, any publicly known electrically conducting material can be used. Specific examples include metal materials such as copper and nickel; and carbon materials such as graphite (e.g., natural graphite and artificial graphite), carbon black (e.g., acetylene black), and amorphous carbon (e.g., needle coke). These may be used alone or in any combination of two or more thereof at any ratio. The conducting material is used such that its content in the positive electrode active material layer is usually 0.01% by mass or higher, preferably 0.1% by mass or higher, and more preferably 1% by mass or higher. At the same time, the content is usually 50% by mass or lower, preferably 30% by Ross or lower, and more preferably 15% by mass or lower. If the content is lower than the above range, the conductivity may be insufficient. Conversely, if the content is higher than the above range, the battery capacity may decrease.

As for a solvent for forming slurry, any type of solvent can be used and it may be either an aqueous or organic solvent as long as it can dissolve or disperse the positive electrode active materials, conducting materials, and binding agent, as well as thickeners that are used as needed. Examples of aqueous solvents include water and a mixture of water and alcohol. Examples of organic solvents include aliphatic hydrocarbons such as hexane; aromatic hydrocarbons such as benzene, toluene, xylene, and methylnaphthalene; heterocyclic compounds such as quinoline and pyridine; ketones such as acetone, methyl ethyl ketone, and cyclohexanone; esters such as methyl acetate and methyl acrylate; amines such as diethylenetriamine and N,N-dimethylaminopropylamine; ethers such as diethyl ether, propylene oxide, and tetrahydrofuran (THF); amides such as N-methylpyrrolidone (NMP), dimethylformamide, and dimethylacetamide; and aprotic polar solvents such as hexamethylphosphoramide and dimethyl sulfoxide.

Examples of materials of the current collector for the positive electrode include metal materials such as aluminium, titanium, tantalum, stainless steel, nickel, and like other metals, and alloys of these metals; and carbon materials such as carbon cloth and carbon paper. Among these, the metal materials, particularly aluminium and its alloy, are preferred.

Examples of the shape of the current collector formed from metal materials include metal foil, metal columnar, metal coil, metal plate, metal thin film, expanded metal, punched metal, and foamed metal. Examples of the shape of the current collector formed from carbon materials include a carbon plate, carbon thin film, and carbon columnar. Among these, a metal thin film is preferred. The thin film may be appropriately formed in mesh. The thin film may have any thickness. Yet, the thickness is usually 1 µm or more, preferably 3 µm or more, and more preferably 5 µm or more. At the same time, it is usually 1 mm or less, preferably 100 µm or less, and more preferably 50 µm or less. If the thin film is thinner than this range, the strength that the film must have as the current collector may be insufficient. Conversely, if the thin film is thicker than this range, handling characteristics may be impaired.

In addition, it is also preferred that surface of the current collector be coated with a conductive additive, for reducing electronic contact resistance between the current collector and the positive electrode active material layer. Examples of conductive additives include carbon and noble metals such as gold, platinum, and silver.

The thickness ratio between the current collector and the positive electrode active material layer is not particularly limited. Yet, the value of the ratio {(thickness of the positive electrode active material layer on one side immediately before injection of the electrolyte solution)/(thickness of the current collector)} is preferably 20 or less, more preferably 15 or less, and most preferably 10 or less. At the same times, it is preferably 0.5 or more, more preferably 0.8 or more, and most preferably 1 or more. If the ratio is more than this range, the current collector may generate heat due to Joule heat during charging and discharging at high current density. If the ratio is less than this range, the volume ratio of the current collector relative to the positive electrode active material may increase, and the battery capacity may decrease.

The positive electrode may be produced by a common method. For example, the positive electrode active material is blended with the above-mentioned binding agent, thickener, conducting material, solvent, and the like to obtain a positive electrode mixture in a slurry form. This mixture is then applied to the current collector, followed by drying, and then is pressed into high density, The pressing into high density can be performed using a hand press, roller press, or the like. The density of the positive electrode active material layer is preferably 1.5 $g/cm^3$ or more, more preferably 2 $g/cm^3$ or more, and still more preferably 2.2 $g/cm^3$ or more. At the same time, it is preferably 5 $g/cm^3$ or less, more preferably 4.5 $g/cm^3$ or less, and still more preferably 4 $g/cm^3$ or less. If the density is more than this range, the permeability of the electrolyte solution in the vicinity of the interface between the current collector and the active material will decrease. In particular, the charge-discharge characteristics at high current density may decrease, and thus high output may not be obtained. If the density is less than this range, the conductivity between the active materials will decrease, thus increasing the battery resistance. Thus, high output may not be obtained.

When using the electrolyte solution of the present invention, the area of the positive electrode active material layer is preferably greater than the outer surface area of an external case of the battery, for achieving high output and increasing the stability at a high temperature. Specifically, the area ratio of the total positive electrode area relative to the surface area of the external case of the secondary battery is preferably at least 15 to 1, and more preferably at least 40 to 1. In the case where the external case of the battery has a prismatic shape with a bottom, the outer surface area refers to the total area calculated from the dimensions (height, width, and depth) of a case portion containing power generating elements, excluding terminal protrusions. In the case where the external case is a cylindrical shape with a bottom, the outer surface area refers to the geometric surface area of a case portion containing power generating elements, excluding terminal protrusions, as determined by approximating the shape of the case portion to a cylinder. The total positive electrode area refers to the geometric surface area of a positive electrode mixture layer, which is opposed to a mixture layer containing the negative electrode active material. In the case of a structure in which the positive electrode mixture layer is formed at both sides of a current collector foil, the area of each positive electrode mixture layer is separately calculated, and these values are added to determine the total positive electrode area.

The thickness of the positive electrode plate is not particularly limited. Yet, for high capacity and high output, the lower limit of the thickness of the mixture layer (excluding the thickness of a metal foil as the core) on each side of the current collector is preferably 10 µm or more, and more preferably 20 µm or more; and at the same time, it is preferably 500 µm or less, and more preferably 450 µm or less.

In addition, the positive electrode active material in which a material having a different composition is attached to the surface thereof may be used. Examples of surface-attached materials include oxides such as aluminium oxide, silicon oxide, titanium oxide, zirconium oxide, magnesium oxide, calcium oxide, boron oxide, antimony oxide, and bismuth oxide; sulfates such as lithium sulfate, sodium sulfate, potassium sulfate, magnesium sulfate, calcium sulfate, and aluminum sulfate; carbonates such as lithium carbonate, calcium carbonate, and magnesium carbonate; and carbon.

<Negative Electrode>

The negative electrode includes a negative electrode mixture containing a negative electrode active material, and a current collector.

Examples of the negative electrode active material include carbonaceous materials capable of storing and releasing lithium such as pyrolysis products of organic materials obtainable under various pyrolysis conditions, artificial graphite, and natural graphite; metal oxide materials capable of storing and releasing lithium such as tin oxide and silicon oxide; lithium metals; various lithium alloys; and lithium-containing metal composite oxide materials. These negative electrode active materials may be used in combination of two or more thereof.

The carbonaceous material capable of storing and releasing lithium is preferably artificial graphite produced by a high-temperature treatment of a graphitizable pitch obtained from various materials or purified natural graphite; or preferably a product obtained by carbonizing these graphite materials after they are surface-treated with pitch or other organic materials. For good balance of initial irreversible capacity and charge-discharge characteristics at high current density, a more preferred carbonaceous material is one selected from the following carbonaceous materials: natural graphite, artificial graphite, a carbonaceous material obtained by performing heat treatment once or more on an artificial carbonaceous material and an artificial graphite material at a temperature in the range of 400° C. to 3200° C.; a carbonaceous material giving a negative electrode active material layer that is composed of at least two or more carbonaceous substances differing in the crystallinity and/or has an interface at which the carbonaceous substances differing in the crystallinity are in contact with each other; a carbonaceous material giving a negative electrode active material layer that is composed of at least two or more carbonaceous substances differing in the orientation and/or has an interface at which the carbonaceous substances differing in the orientation are in contact with each other. These carbon materials may be used alone or in any combination of two or more thereof at any ratio.

Examples of the carbonaceous material obtained by performing heat treatment once or more on an artificial carbonaceous material and an artificial graphite material at a temperature in the range of 400° C. to 3200° C. include natural graphite, coal coke, petroleum coke, coal pitch, petroleum pitch, oxidation-treated coal pitch, oxidation-treated petroleum pitch, needle coke, pitch coke, carbon materials obtained by partially graphitizing needle coke and pitch coke, pyrolysis products of organic materials such as furnace black, acetylene black, and pitch carbon fibers, carbonizable organic materials and carbides thereof, solutions obtained by dissolving carbonizable organic materials in low molecular weight organic solvents such as benzene, toluene, xylene, quinoline, and n-hexane, and carbides thereof.

Metal materials (excluding lithium-titanium composite oxides) used as the negative electrode active materials are not particularly limited as long as they can store and release lithium. Any of the following compounds may be used: elemental lithium; elemental metals and alloys for forming lithium alloys; and compounds such as oxides, carbides, nitrides, silicides, sulfides, and phosphides of these elemental metals and alloys. As for the elemental metals and alloys for forming lithium alloys, materials containing metals and metalloid elements in groups 13 and 14 of the periodic table are preferred. Elemental metals such as aluminium, silicon, and tin (hereinafter, these elements are referred to as "specific metallic element" for abbreviation) and alloys or compounds containing these atoms are more preferred. These may be used alone or in any combination of two or more thereof at any ratio.

Examples of negative electrode active materials containing at least one atom selected from the specific metallic elements include the following: any specific metallic element in its elemental form; alloys consisting of two or more specific metallic elements; compounds containing one or two or more specific metallic elements and one or two or more other metal elements; compounds containing one or two or more specific metallic elements; and composite compounds such as oxides, carbides, nitrides, silicides, sulfides, and phosphides thereof. The use of any of these elemental metals, alloys, and metal compounds as the negative electrode active material enables to increase the battery capacity.

In addition, compounds in which above-described composite compounds are intricately bound to elemental metals, alloys, non-metallic elements, and like other various elements may also be used as the negative electrode active materials. Specifically, in the case where silicon and tin are used as the elemental metals, for example, alloys consisting of these elements and other metals that do not act as negative electrodes can be used. For example, in the case of tin, a composite compound containing 5 or 6 different elements in combination of tin, a metal (other than tin and silicon) that acts as the negative electrode, a metal that does not act as the negative electrode, and a non-metallic element can be used.

Specific examples include elemental Si, $SiB_4$, $SiB_6$, $Mg_2Si$, $Ni_2Si$, $TiSi_2$, $MoSi_2$, $CoSi_2$, $NiSi_2$, $CaSi_2$, $CrSi_2$, $Cu_6Si$, $FeSi_2$, $MnSi_2$, $NbSi_2$, $TaSi_2$, $VSi_2$, $WSi_2$, $ZnSi_2$, SiC, $Si_3N_4$, $Si_2N_2O$, $SiO_v$ ($0<v\leq2$), LiSiO or elemental tin, $SnSiO_3$, LiSnO, $Mg_2Sn$, and $SnO_w$ ($0<w\leq2$).

In addition, a composite material containing Si or Sn as a first constituent element and other elements as second and third constituent elements can also be used. The second constituent element is, for example, at least one selected from cobalt, iron, magnesium, titanium, vanadium, chrome, manganese, nickel, copper, zinc, gallium, and zirconium. The third constituent element is, for example, at least one selected from boron, carbon, aluminium, and phosphorus.

In particular, for achieving high battery capacity and excellent battery characteristics, the metal material is preferably elemental silicon or tin (which may contain traces of impurities), $SiO_v$ ($0<v\leq2$), $SnO_w$ ($0\leq w\leq2$), Si—Co—C composite material, Si—Ni—C composite material, Sn—Co—C composite material, and Sn—Ni—C composite material.

Any lithium-containing metal composite oxide material can be used as the negative electrode active material as long as it can store and release lithium. Yet, in terms of charge-discharge characteristics at high current density, a material containing titanium and lithium is preferred; a lithium-containing composite metal oxide material containing titanium is more preferred; and a composite oxide of lithium and titanium (hereinafter referred to as "lithium-titanium composite oxide" for abbreviation) is still more preferred. Specifically, the use of a lithium-titanium composite oxide having a spinel structure in the negative electrode active material for the electrolyte battery is particularly preferred because it contributes to a significant decrease in output resistance.

The lithium-titanium composite oxide is preferably a compound represented by formula (J):

$$Li_x Ti_y M_z O_4 \quad (J)$$

in formula (J), M represents at least one element selected from the group consisting of Na, K, Co, Al, Fe, Ti, Mg, Cr, Ga, Cu, Zn, and Nb.

Among the compositions represented by the above formula (J), structures shown below are particularly preferred for good balance of battery performance.

$$1.2 \leq x \leq 1.4, 1.5 \leq y \leq 1.7, z=0 \quad (i)$$

$$0.9 \leq x \leq 1.1, 1.9 \leq y \leq 2.1, z=0 \quad (ii)$$

$$0.7 \leq x \leq 0.9, 2.1 \leq y \leq 2.3, z=0 \quad (iii)$$

The particularly preferred compositions of the above compound are typically as follows: (i) $Li_{4/3}Ti_{5/3}O_4$; (ii) $Li_1Ti_2O_4$; and (iii) $Li_{4/5}Ti_{11/5}O_4$. As for the structure wherein Z≠0, preferred examples include $Li_{4/3}Ti_{4/3}Al_{1/3}O_4$.

Preferably, the negative electrode mixture further contains a binding agent, a thickener, and a conducting material.

Examples of the binding agent include those listed as examples of the binding agent that can be used in the positive electrode. The percentage of the binding agent relative to the negative electrode active material is preferably 0.1% by mass or more, more preferably 0.5% by mass or more, and particularly preferably 0.6% by mass or more. At the same time, it is preferably 20% by mass or less, more preferably 15% by mass or less, still more preferably 10% by mass or less, and particularly preferably 8% by mass or less. If the percentage of the binding agent relative to the negative electrode active material is more than the above range, the percentage of the binding agent that does not contribute to the battery capacity will increase, which may cause a decrease in the battery capacity. If the percentage is less than the above range, it may cause a decrease in the strength of the negative electrode.

In particular, in the case where a rubber-like polymer as typified by SBR is used as a main component, the percentage of the binding agent relative to the negative electrode active material is usually 0.1% by mass or more, preferably 0.5% by mass or more, and more preferably 0.6% by mass or more. At the same time, it is usually 5% by mass or less, preferably 3% by mass or less, and more preferably 2% by mass. In the case where a fluorinated polymer as typified by polyvinylidene fluoride is used as a main component, the percentage of the binding agent relative to the negative electrode active material is usually 1% by mass or more, preferably 2% by mass or more, and more preferably 3% by mass or more. At the same time, it is usually 15% by mass or less, preferably 10% by mass or less, and more preferably 8% by mass or less.

Examples of the thickener include those listed as examples of the thickener that can be used for the positive electrode. The percentage of the thickener relative to the negative electrode active material is usually 0.1% by mass or more, preferably 0.5% by mass or more, and more preferably 0.6% by mass or more. At the same time, it is usually 5% by mass or less, preferably 3% by mass or less, and more preferably 2% by mass or less. If the percentage of the thickener relative to the negative electrode active material is less than the above range, the coating properties may markedly decrease. If the percentage is more than the above range, the percentage of the negative electrode active material occupying the negative electrode active material layer will decrease, which may unfortunately cause a decrease in the battery capacity or an increase in the resistance between the negative electrode active materials.

Examples of conducting materials of the negative electrode include metal materials such as copper and nickel; and carbon materials such as graphite and carbon black.

As for a solvent for forming slurry, any type of solvent can be used and it may be either an aqueous or organic solvent as long as it can dissolve or disperse the negative electrode active materials and binding agents, as well as thickeners and conducting materials that are used as needed.

Examples of aqueous solvents include water and alcohol. Examples of organic solvents include N-methylpyrrolidone (NMP), dimethylformamide, dimethylacetamide, methyl ethyl ketone, cyclohexanone, methyl acetate, methyl acrylate, diethyltriamine, N,N-dimethylaminopropylamine, tetrahydrofuran (THF), toluene, acetone, diethyl ether, dimethylacetamide, hexamethylphosphoramide, dimethyl sulfoxide, benzene, xylene, quinoline, pyridine, methylnaphthalene, and hexane.

Examples of materials of the negative electrode current collector include copper, nickel, and stainless steel. Among these, copper is preferred because it can be easily processed into a thin film, and also in terms of cost.

The thickness of the current collector is usually 1 μm or more, and preferably 5 μm or more; and it is usually 100 μm or less, and preferably 50 μm or less. If the negative electrode current collector is too thick, the total battery capacity may excessively decrease. Conversely, if it is too thin, handling may be difficult.

The negative electrode can be produced by a common method. For example, the negative electrode active material is blended with the above-mentioned binding agent, thickener, conducting material, solvent, and the like to obtain a mixture in a slurry form. This mixture is then applied to the current collector, followed by drying. Then, it is pressed into high density. In the case of using alloy materials, a method of forming a thin film layer containing the negative electrode active materials (i.e., negative electrode active material layer) by deposition, sputtering, plating, or the like is used.

The structure of the electrode formed from the negative electrode active materials is not particularly limited, and the density of the negative electrode active materials present on the current collector is preferably 1 g·cm$^{-3}$ or more, more preferably 1.2 g·cm$^{-3}$ or more, and particularly preferably 1.3 g·cm$^{-3}$ or more. At the same time, it is preferably 2.2 g·cm$^{-3}$ or less, more preferably 2.1 g·cm$^{-3}$ or less, still more preferably 2.0 g·cm$^{-3}$ or less, and particularly preferably 1.9 g·cm$^{-3}$ or less. If the density of the negative electrode active materials present on the current collector is more than the above range, the negative electrode active material particles may be destroyed, which may cause an increase in the initial irreversible capacity or a decrease in the permeability of the electrolyte solution in the vicinity of the interface between the current collector and the negative electrode active materials, resulting in poor charge-discharge characteristics at high current density. If the density is less than the above range, the conductivity between the negative electrode active materials will decrease. As a result, the battery resistance may increase and the capacity per unit volume may decrease.

The thickness of the negative electrode plate is designed in accordance with the positive electrode plate. While it is not particularly limited, the thickness of the mixture layer (excluding the thickness of a metal foil as the core) is usually 15 µm or more, preferably 20 µm or more, and more preferably 30 µm or more; and at the same time, it is usually 300 µm or less, preferably 280 µm or less, and more preferably 250 µm or less.

In addition, the negative electrode active material in which a material having a different composition is attached to the surface thereof may be used. Examples of surface-attached materials include oxides such as aluminium oxide, silicon oxide, titanium oxide, zirconium oxide, magnesium oxide, calcium oxide, boron oxide, antimony oxide, and bismuth oxide; sulfates such as lithium sulfate, sodium sulfate, potassium sulfate, magnesium sulfate, calcium sulfate, and aluminum sulfate; and carbonates such as lithium carbonate, calcium carbonate, and magnesium carbonate.

<Separator>

Preferably, the lithium-ion secondary battery of the present invention further includes a separator.

The separator can be made from any material and in any form as long as it is stable to the electrolyte solution and is excellent in liquid retentivity. Any publicly known separator can be used. In particular, it is preferred to use a separator formed from materials (such as resin, glass fibers, and inorganic materials) stable to the electrolyte solution of the present invention, and in the form of, for example, a porous sheet or a nonwoven fabric having excellent liquid retentivity.

Examples of materials of resin and glass fiber separators include polyolefin such as polyethylene and polypropylene, aromatic polyamide, polytetrafluoroethylene, polyethersulfone, and glass filter. These materials may be used alone or in any combination of two or more thereof at any ratio, as in a polypropylene/polyethylene two-layer film, a polypropylene/polyethylene/polypropylene three-layer film, or the like. In particular, in terms of favorable permeability of the electrolyte solution and shutdown effects, the separator is preferably a porous sheet, nonwoven fabric, or the like formed from polyolefin such as polyethylene and polypropylene.

The separator may have any thickness. Yet, the thickness is usually 1 µm or more, preferably 5 µm or more, and still more preferably 8 µm or more. At the same time, it is usually 50 µm or less, preferably 40 µm or less, and more preferably 30 µm or less. If the thickness of the separator is excessively smaller than the above range, the insulating properties and the mechanical strength may decrease. If the thickness is excessively larger than the above range, not only the battery performance such as rate characteristics but also the energy density of the entire electrolyte battery may decrease.

Further, in the case where a porous separator such as a porous sheet or a nonwoven fabric is used, the separator may have any porosity. Yet, the porosity is usually 20% or more, more preferably 35% or more, and still more preferably 45% or more. At the same time, it is usually 90% or less, preferably 85% or less, and still more preferably 75% or less. If the porosity is excessively less than the above range, the film resistance tends to increase, resulting in poor rate characteristics. If the porosity is excessively more than the above range, the mechanical strength and insulating property of the separator tend to decrease.

The separator also may have any average pore size. Yet, it is usually 0.5 µm or less, and preferably 0.2 µm or less; and at the same time, it is usually 0.05 µm or more. If the average pore size is more than the above range, a short circuit may easily occur. If the average pore size is less than the above range, the film resistance may increase, resulting in low rate characteristics.

On the other hand, examples of inorganic materials include oxides such as alumina and silicon dioxide; nitride such as aluminum nitride and silicon nitride; and sulfates such as barium sulfate and calcium sulfate. Particulate or fibrous inorganic materials are used.

As for the shape, the separator in the form of a thin film, such as a nonwoven fabric, a woven fabric, or a macroporous film, is used. In the case of the separator in the form of a thin film, the separator preferably has a pore size of 0.01 to 1 µm and a thickness of 5 to 50 µm. Besides the independent separator in the form of a thin film, it is possible to use a separator in which a composite porous layer containing particles of the inorganic material is formed on the surface layer of the positive electrode and/or negative electrode, using a resin binding agent. For example, a porous layer of alumina particles having a 90% particle size of less than 1 µm may be formed on the both surfaces of the positive electrode, using fluororesin as a binding agent.

<Battery Design>

The electrode group may have either one of the following structures: a layered structure in which the positive electrode plate and the negative electrode plate are layered with the separator therebetween; and a coiled structure in which the positive electrode plate and the negative electrode plate are spirally wound with the separator therebetween. The percentage of the volume of the electrode group occupying the internal volume of the battery (hereinafter, this percentage is referred to as "electrode group occupancy") is usually 40% or higher, and preferably 50% or higher; and at the same time, it is usually 90% or lower, and preferably 80% or lower.

If the electrode group occupancy is lower than the above range, the battery capacity will decrease. If the electrode group occupancy is higher than the above range, the temperature of the battery will be high due to limited void space. As a result, components may expand and the vapor pressure of the liquid component of the electrolyte may increase, thus increasing the internal pressure and decreasing various battery characteristics such as charge-discharge repetition performance and high-temperature storage. Moreover, a gas release valve through which the internal pressure is released to the outside may be put into operation.

The structure of the current collector is not particularly limited. Yet, in order to more effectively improve the charge-discharge characteristics of the electrolyte solution of the present invention at high current density, the current collector preferably has a structure that reduces the resistance in wiring and joint portions. If the internal resistance is reduced as described above, the effects resulting from the use of the electrolyte solution of the present invention will be achieved in a particularly favorable manner.

In the case where the electrode group has the layered structure, a structure formed by bundling metal core portions of the electrode layers and welding the bundle to a terminal is suitably used. If the electrode area of one sheet is large, the internal resistance will be high. Thus, it is preferred to provide plural terminals in the electrode so as to reduce the resistance. In the case where the electrode group has the coiled structure described above, the internal resistance can be reduced by providing plural lead structures for each of the positive electrode and the negative electrode and then bundling them into a terminal.

Any material can be used for the external case as long as it is a material stable to the electrolyte solution. Specific examples include metals such as nickel-plated steel plates, stainless steel, aluminium, aluminium alloy, and magnesium alloy; and laminated films of resin and aluminum foil. For reducing weight, metals such as aluminum and aluminum alloy, and laminated films are suitably used.

Examples of the external oases formed from metals include one having a hermetically sealed structure formed by welding metals together by laser welding, resistance welding, or ultrasonic welding; and one having a caulking structure formed from the above-described metals with a resin gasket. Examples of the external case formed from the laminated film include one having a hermetically sealed structure formed by heat-sealing resin layers together. In order to enhance the sealing properties, a resin different from the resin used for the laminated film may be interposed between the resin layers. In particular, in the case where a hermetic structure is formed by heat-sealing resin layers together with a collector terminal, the process involves joining of the metal and resin. Thus, a resin having a polar group or a modified resin having a polar group introduced thereinto is suitably used as a resin to be interposed.

The lithium-ion secondary battery of the present invention may have any shape. Examples include a cylindrical shape, a prismatic shape, a laminated shape, a coin shape, and a large type. The shapes and structures of the positive electrode, negative electrode, and separator can be modified in accordance with each battery shape for use.

Still another aspect of the present invention is a module including the lithium-ion secondary battery of the present invention.

The present invention also provides an electric double-layer capacitor including a positive electrode, a negative electrode, and the electrolyte solution.

In the electric double-layer capacitor of the present invention, at least one of the positive electrode and the negative electrode is a polarizable electrode, and the below-described electrodes (described in detail in JP-A H09-7896) can be used as the polarizable electrode and the non-polarizable electrode.

The polarizable electrode of the present invention, which mainly includes active carbon, preferably includes inactivated carbon having a large specific surface area and a conducting agent (such as carbon black) that imparts electron conductivity. The polarizable electrode can be formed by various methods. For example, a polarizable electrode including activated carbon and carbon black can be formed by mixing activated carbon powder, carbon black, and a phenolic resin, press-molding the mixture, and then firing and activating the mixture in an inert gas atmosphere and in a steam atmosphere. Preferably, the polarizable electrode is joined with the current collector by the use of a conductive adhesive or the like.

Alternatively, activated carbon powder, carbon black, and a binder can be mixed and kneaded into the form of a sheet in the presence of an alcohol, followed by drying, whereby a polarizable electrode is obtained. As for the binder, polytetrafluoroethylene is used, for example. In addition, activated carbon powder, carbon black, a binder, and a solvent can be mixed to obtain slurry, and the metal foil of the current collector is coated with the slurry, followed by drying, whereby a polarizable electrode integrally formed with the current collector is obtained.

The electric double-layer capacitor may have a structure in which the polarizable electrode mainly including activated carbon is used for both electrodes. Alternatively, the electric double-layer capacitor may have a structure in which a non-polarizable electrode is used on one side. Examples of such structures include one in which a positive electrode mainly including metal oxide or the like as the electrode active material is combined with a polarized negative electrode mainly including activated carbon; and one in which a negative electrode mainly including a carbon material capable of reversibly storing and releasing lithium ions or a negative electrode formed from lithium metal or lithium alloy is combined with a polarizable electrode mainly including activated carbon.

In addition, carbonaceous materials such as carbon black, graphite, expanded graphite, porous carbon, carbon nanotube, carbon nanohorn, and Ketjen black may be used, instead of or in combination with activated carbon.

The non-polarizable electrode is preferably one mainly including a carbon material capable of reversibly storing and releasing lithium ions, and the carbon material in which lithium ions are stored is used as the electrode. In this case, a lithium salt is used as the electrolyte. An electric double-layer capacitor having the above structure will have higher withstand voltage that exceeds 4 V.

A solvent used to prepare slurry during production of the electrode is preferably one in which the binder is soluble, and one of the following solvents is suitably selected according to the type of the binder: N-methylpyrrolidone, dimethylformamide, toluene, xylene, isophorone, methyl ethyl ketone, ethyl acetate, methyl acetate, dimethyl phthalate, ethanol, methanol, butanol, and water.

Examples of activated carbon used as the polarizable electrode include phenolic resin-based activated carbon, coconut shell-based activated carbon, and petroleum coke-based activated carbon. Among these, the use of petroleum coke-based activated carbon or phenolic resin-based activated carbon is preferred for providing high capacity. In addition, activated carbon can be obtained by an activating method, such as steam activation and melting KOH activation. The use of activated carbon obtained by melting KOH activation is preferred for providing higher capacity.

Examples of preferred conducting agents to be used for the polarizable electrode include carbon black, Ketjen black, acetylene black, natural graphite, artificial graphite, metal fiber, conductive titanium oxide, and ruthenium oxide. The conducting agent such as carbon black to be used in the polarizable electrode is preferably mixed in an amount of 1 to 50% by mass in the total amount of the conducting agent and the activated carbon, for providing good conductivity (low internal resistance). If the amount is too large, the resulting product will have decreased capacity.

The activated carbon to be used as the polarizable electrode is preferably activated carbon having an average particle size of 20 μm or less and a specific surface area of 1500 to 3000 $m^2/g$, for providing an electric double-layer capacitor having high capacity and low internal resistance. In addition, examples of preferred carbon materials for constituting an electrode mainly including a carbon material capable of reversibly storing and releasing lithium ions include natural graphite, artificial graphite, graphitized mesocarbon microbeads, graphitized whiskers, vapor-grown carbon fibers, calcined products of furfuryl alcohol resin, and calcined products of novolac resin.

Any current collector can be used as long as it is chemically and electrochemically corrosive-resistant. The current collector as the polarizable electrode mainly including activated carbon is preferably formed from stainless steel, aluminium, titanium, or tantalum. Among these, stainless steel and aluminium are particularly preferred materials in terms of both characteristics and cost of the resulting electric double-layer capacitor. The current collector as the electrode mainly including a carbon material capable of reversibly storing and releasing lithium ions is preferably formed from stainless steel, copper, or nickel.

Lithium ions can be stored, in advance, in a carbon material capable of reversibly storing and releasing lithium ions by the following methods: (1) a method in which lithium powder is mixed into a carbon material capable of reversibly storing and releasing lithium ions; (2) a method in which a lithium foil is placed on an electrode formed from a binder and a carbon material capable of reversibly storing and releasing lithium ions to establish an electrical contact between the lithium foil and the electrode; the electrode is immersed in an electrolyte solution in which a lithium salt is dissolved so as to ionize the lithium; and lithium ions are incorporated into the carbon material; and (3) a method in which an electrode formed from a binder and a carbon material capable of reversibly storing and releasing lithium ions is placed on the negative side, and a lithium metal is placed on the positive side; the electrode and the lithium metal are immersed in a non-aqueous electrolyte solution containing a lithium salt as the electrolyte; and an electrical current is applied to electrochemically introduce ionized lithium ions into the carbon material.

As the electric double-layer capacitor, for example, a winding electric double-layer capacitor, a laminated electric double-layer capacitor, and a coin-shaped electric double-layer capacitor are commonly known. The electric double-layer capacitor of the present invention can be formed in any of these capacitors.

For example, the winding electric double-layer capacitor is assembled by the following method: a positive electrode and a negative electrodes each including a current collector and a laminated body (electrode) of electrode layers are wound together with a separator therebetween to produce a winding element; the winding element is placed in an aluminum case, for example; the case is filled with an electrolyte solution, preferably, a non-aqueous electrolyte solution; and then the case is sealed with a sealing member made of rubber.

As for the separator, one formed from conventionally known materials and having a conventionally known structure can be used in the present invention. Examples include polyethylene porous films and nonwoven fabric of polypropylene fibers, glass fibers, or cellulose fibers.

In addition, a conventional method may be employed to produce a laminated electric double-layer capacitor in which a sheet-like positive electrode and a sheet-like negative electrode are laminated with an electrolyte and a separator interposed therebetween; or to produce a coin-shaped electric double-layer capacitor in which a positive electrode and a negative electrode are fixed in a coin shape using a gasket with an electrolyte and a separator interposed therebetween.

As described above, the use of the electrolyte solution of the present invention enables to achieve a secondary battery having excellent high-temperature storage characteristics, a module including the secondary battery, and an electric double-layer capacitor.

EXAMPLES

The present invention is described in further detail below based on examples and comparative examples, but the present invention is not limited to these examples only.

Examples 1 to 22 and Comparative Examples 1 to 6

(Preparation of an Electrolyte Solution)

Components were mixed to obtain the composition of Table 1. Then, $LiPF_6$ was added to the mixture to a concentration of 1.0 mol/L, whereby an electrolyte solution was obtained.

The compounds shown in the table are as follows.
a: $CF_3CH_2OCOOCH_3$
b: $CF_3CH_2OCOOCH_2CF_3$
FEC: monofluoroethylene carbonate
DEC: diethyl carbonate
<HF Content>

The HF content in the electrolyte solution obtained above was measured by neutralization titration. Table 1 shows the results.
<Oxidation Resistance>
(Measurement of the Potential Window)

The electrolyte solution obtained above was injected into a three electrode cell for voltage measurement (working electrode: platinum; counter electrode: Li; reference electrode: Li; HS cell available from Hohsen Corporation). The potential was swept at 5 mV/sec using a potentiostat at 25° C., and the decomposition current was measured (linear sweep voltammetry: LSV). The voltage when the current value was 0.3 mA/cm$^2$ was regarded as decomposition point. Table 1 shows the measurement results.
<High-Temperature Storage Characteristics>
(Production of a Coin-Shaped Battery)

$LiNi_{1/3}Mn_{1/3}CO_{1/3}O_2$, carbon black, and polyvinylidene fluoride (product name: KF-7200 available from Kureha Corporation) were mixed at a mass ratio of 92/3/5 to obtain a positive electrode active material, which was then dispersed in N-methyl-2-pyrrolidone to obtain slurry. Thereby, positive electrode mixture slurry was prepared. The positive electrode mixture slurry was uniformly applied to the aluminum current collector and dried into a positive electrode mixture layer (thickness of 50 μm), which was then press-molded with a roller press. Thereby, a positive electrode stack was produced. The positive electrode stack was punched out to a size of 1.6 mm in diameter with a punching machine. Thus, a circular positive electrode was produced.

Separately, styrene-butadiene rubber dispersed in distillated water was added to artificial graphite powder such that the amount of solids was 6% by mass. The resulting mixture was mixed with a disperser to form slurry. The slurry was uniformly applied to the negative electrode current collector (copper foil having a thickness of 10 μm), and dried. Thereby, a negative electrode mixture layer was formed. Subsequently, the negative electrode mixture layer was press-molded with a roller press, and the molded product was punched out to a size of 1.6 mm in diameter with a punching machine. Thus, a circular negative electrode was produced.

The circular positive electrode was placed so as to face the negative electrode with a microporous polyethylene film (separator) having a thickness of 20 μm interposed therebetween, and the electrolyte solution obtained above was injected. After the electrolyte solution sufficiently permeated the separator and the like, sealing, pre-charging, and aging were carried out. Thereby, a coin-shaped lithium-ion secondary battery was produced.
(Measurement of the Battery Characteristics)

The coin-shaped lithium-ion secondary battery was tested for high-temperature storage characteristics in the following procedure.
(Charge and Discharge Conditions)

Charge: maintaining 0.5 C and 4.4 V until the charging current reached 1/10 C (CC-CV charge)

Discharge: 0.5 C, with 3.0 V cut-off (CC discharge)
(High-Temperature Storage Characteristics)

In regard to the high-temperature storage characteristics, the battery was charged and discharged under the above-described charge-discharge conditions (charged at 1.0 C and a predetermined voltage until the charging current reached ⅒ C, and discharged at a current corresponding to 1 C until the voltage reached 3.0 V), and the discharge capacity was examined. Subsequently, the battery was again charged under the above charging conditions, and stored in a constant-temperature bath maintained at 85° C. for 1 day. After storage, the battery was discharged at 25° C. under the above discharging conditions to the discharge cut-off voltage of 3 V, and the remaining capacity was measured. Further, the battery was charged under the above charging conditions. Then, the battery was discharged at a constant current under the above discharging conditions to the discharge cut-off voltage of 3 V, and the recovery capacity was measured. Table 1 shows the recovery capacity ratio, with the discharge capacity before storage as 100.

TABLE 1

|  | Composition (mass ratio) | Concentration of b in the solvent (mass %) | a/b (mass ratio) | HF content (ppm) | Oxidation resistance (V) | High-temperature storage characteristics Recovery capacity ratio (%) |
|---|---|---|---|---|---|---|
| Example 1 | FEC/DEC/a + b (31.3/6.8/61.9) | 61.3 | 0.01 | 10 | 4.93 | 93 |
| Example 2 | FEC/DEC/a + b (30.1/0/69.9) | 69.2 | 0.01 | 10 | 4.94 | 92 |
| Example 3 | FEC/DEC/a + b (32.4/14/53.6) | 53.1 | 0.01 | 10 | 4.92 | 93 |
| Example 4 | FEC/DEC/a + b (33.6/21.8/44.6) | 44.2 | 0.01 | 10 | 4.91 | 93 |
| Example 5 | FEC/DEC/a + b (34.9/30.3/34.8) | 34.5 | 0.01 | 10 | 4.91 | 92 |
| Example 6 | FEC/DEC/a + b (36.4/39.4/24.2) | 24.0 | 0.01 | 10 | 4.90 | 91 |
| Example 7 | FEC/DEC/a + b (49.4/39.4/11.2) | 11.1 | 0.01 | 10 | 4.90 | 88 |
| Example 8 | FEC/DEC/a + b (20.4/0/79.6) | 78.8 | 0.01 | 10 | 4.94 | 91 |
| Comparative Example 1 | FEC/DEC/a + b (39.7/60.3/0) | 0 | — | 10 | 4.78 | 82 |
| Comparative Example 2 | FEC/DEC/a + b (39.5/59.1/1.4) | 1.38 | 0.01 | 10 | 4.80 | 85 |
| Comparative Example 3 | FEC/DEC/a + b (9.1/0/90.9) | 90 | 0.01 | 10 | 4.94 | 84 |
| Comparative Example 4 | FEC/DEC/a + b (32.1/6.9/61) | 33.9 | 0.8 | 10 | 4.91 | 89 |
| Comparative Example 5 | FEC/DEC/a + b (31.2/6.9/61.9) | 61.9 | 0 | 10 | 4.92 | 88 |
| Comparative Example 6 | FEC/DEC/a + b (36.7/39.8/23.5) | 23.5 | 0 | 10 | 4.88 | 88 |
| Example 9 | FEC/DEC/a + b (32.0/6.9/61.1) | 59.3 | 0.03 | 100 | 4.85 | 78 |
| Example 10 | FEC/DEC/a + b (32.1/6.9/61) | 43.6 | 0.4 | 10 | 4.92 | 89 |
| Example 11 | FEC/DEC/a + b (31.2/6.7/62.1) | 56.4 | 0.1 | 10 | 4.93 | 91 |
| Example 12 | FEC/DEC/a + b (31.2/6.7/62.1) | 60.9 | 0.02 | 10 | 4.93 | 92 |
| Example 13 | FEC/DEC/a + b (31.2/6.7/62.1) | 62.0 | 0.001 | 10 | 4.93 | 92 |
| Example 14 | FEC/DEC/a + b (36.7/39.8/23.5) | 13.1 | 0.8 | 10 | 4.89 | 89 |
| Example 15 | FEC/DEC/a + b (36.7/39.8/23.5) | 15.6 | 0.5 | 10 | 4.90 | 90 |
| Example 16 | FEC/DEC/a + b (36.7/39.8/23.5) | 23.0 | 0.02 | 10 | 4.90 | 91 |
| Example 17 | FEC/DEC/a + b (36.7/39.8/23.5) | 23.5 | 0.0001 | 10 | 4.89 | 90 |
| Example 18 | FEC/DEC/a + b (31.3/6.8/61.9) | 60.2 | 0.03 | 0.5 | 4.89 | 90 |
| Example 19 | FEC/DEC/a + b (31.3/6.8/61.9) | 60.2 | 0.03 | 1 | 4.90 | 91 |
| Example 20 | FEC/DEC/a + b (31.3/6.8/61.9) | 60.2 | 0.03 | 2.5 | 4.92 | 93 |
| Example 21 | FEC/DEC/a + b (31.3/6.8/61.9) | 60.2 | 0.03 | 30 | 4.90 | 92 |
| Example 22 | FEC/DEC/a + b (31.3/6.8/61.9) | 60.2 | 0.03 | 60 | 4.90 | 91 |
| Example 23 | FEC/DEC/a + b (31.2/6.7/62.1) | 62.1 | 0.0001 | 10 | 4.93 | 91 |

The table shows that the electrolyte solutions of the examples are excellent in oxidation resistance and high-temperature storage characteristics.

INDUSTRIAL APPLICABILITY

The electrolyte solution of the present invention is suitably applicable as an electrolyte solution for a lithium-ion secondary battery.

The invention claimed is:
1. An electrolyte solution comprising:
a solvent; and
an electrolyte salt,
the solvent containing a fluorine-containing compound (A) represented by formula (1) shown below in an amount of 0.01 to 20% by mass and a fluorine-containing compound (B) represented by formula (2) shown below in an amount of 20 to 80% by mass:

$$Rf^1OCOOR \quad (1)$$

wherein $Rf^1$ is a C1-C4 fluorine-containing alkyl group, and R is a C1-C4 non-fluorinated alkyl group, and

$$Rf^2OCOORf^3 \quad (2)$$

wherein $Rf^2$ and $Rf^3$ are the same or different, and each is a C1-C4 fluorine-containing alkyl group,
wherein the fluorine-containing compound (A) is at least one compound selected from the group consisting of $CF_3CH_2OCOOCH_3$, $CF_3CH_2OCOOCH_2CH_3$, $CF_3CF_2CH_2OCOOCH_3$, and $CF_3CF_2CH_2OCOOCH_2CH_3$; and the fluorine-containing compound(B) is at least one compound selected from the group consisting of $CF_3CH_2OCOOCH_2CF_3$, $CF_2HCF_2CH_2OCOOCH_2CF_2CF_2H$, and $(CF_3)_2CHOCOOCH(CF_3)_2$.

2. The electrolyte solution according to claim 1, wherein the fluorine-containing compound (A) is at least one compound selected from the group consisting of $CF_3CH_2OCOOCH_3$ and $CF_3CH_2OCOOC_2H_5$; and the fluorine-containing compound(B) is $CF_3CH_2OCOOCH_2CF_3$.

3. The electrolyte solution according to claim 1,
wherein the solvent further comprises at least one selected from the group consisting of a non-fluorinated saturated cyclic carbonate, a fluorinated saturated cyclic carbonate, and a non-fluorinated chain carbonate.

4. The electrolyte solution according to claim 3,
wherein the non-fluorinated saturated cyclic carbonate is at least one compound selected from the group consisting of ethylene carbonate, propylene carbonate, and butylene carbonate.

5. The electrolyte solution according to claim 3,
wherein the non-fluorinated chain carbonate is at least one compound selected from the group consisting of dimethyl carbonate, ethyl methyl carbonate, diethyl carbonate, methyl propyl carbonate, methyl butyl carbonate, ethyl propyl carbonate, and ethyl butyl carbonate.

6. The electrolyte solution according to claim 1,
wherein a mass ratio A/B of the fluorine-containing compound (A) to the fluorine-containing compound (B) is less than 1.

7. The electrolyte solution according to claim 1,
wherein the electrolyte salt is at least one lithium salt selected from the group consisting of $LiPF_6$, $LiBF_4$, $LiSO_3CF_3$, $LiN(SO_2CF_3)_2$, $LiN(SO_2C_2F_5)_2$, lithium difluoro(oxalato)borate, lithium bis(oxalato)borate, and a salt represented by a formula: $LiPF_a(C_nF_{2n+1})_{6-a}$ wherein a is an integer of 0 to 5 and n is an integer of 1 to 6.

8. The electrolyte solution according to claim 1,
wherein the electrolyte solution comprises 0.5 to 70 ppm of HF.

9. The electrolyte solution according to claim 1,
wherein the electrolyte solution further comprises at least one compound selected from the group consisting of an unsaturated cyclic carbonate, a fluorinated saturated cyclic carbonate, and a cyclic sulfonic acid compound, in an amount of 0.1 to 10% by mass.

10. An electrochemical device comprising the electrolyte solution as defined in claim 1.

11. A lithium-ion secondary battery comprising the electrolyte solution as defined in claim 1.

12. A module comprising the electrochemical device as defined in claim 10.

* * * * *